(12) United States Patent
Higgins

(10) Patent No.: US 12,397,080 B2
(45) Date of Patent: Aug. 26, 2025

(54) SENSOR SYSTEM FOR A LIGHT FIXTURE HAVING ULTRAVIOLET STERILIZATION FUNCTIONALITY

(71) Applicant: CalyxPure, Inc., Houston, TX (US)

(72) Inventor: John C. Higgins, Houston, TX (US)

( * ) Notice: Subject to any disclaimer, the term of this patent is extended or adjusted under 35 U.S.C. 154(b) by 0 days.

(21) Appl. No.: 18/399,394

(22) Filed: Dec. 28, 2023

(65) Prior Publication Data

US 2024/0123107 A1    Apr. 18, 2024

Related U.S. Application Data

(63) Continuation of application No. 17/317,656, filed on May 11, 2021, now abandoned.

(51) Int. Cl.
*A61L 9/20* (2006.01)

(52) U.S. Cl.
CPC ............ *A61L 9/20* (2013.01); *A61L 2209/111* (2013.01); *A61L 2209/12* (2013.01)

(58) Field of Classification Search
None
See application file for complete search history.

(56) References Cited

U.S. PATENT DOCUMENTS

| | | |
|---|---|---|
| 3,670,193 A | 6/1972 | Thorington et al. |
| 3,992,646 A | 11/1976 | Corth |
| 5,012,609 A | 5/1991 | Ignatius et al. |
| 5,278,432 A | 1/1994 | Ignatius et al. |
| 6,242,752 B1 | 6/2001 | Soma et al. |

(Continued)

FOREIGN PATENT DOCUMENTS

| | | |
|---|---|---|
| CA | 2856725 | 6/2013 |
| CN | 201797809 | 4/2011 |

(Continued)

OTHER PUBLICATIONS

Argyroudi-Akoyunoglou et al., "Photoinduced Changes in the Chlorophyll a to Chlorophyll b Ratio in Young Bean Plants," Plant Physiology, Aug. 1970, 46(2), pp. 247-249.

(Continued)

*Primary Examiner* — Andrew Smyth
(74) *Attorney, Agent, or Firm* — Adair Myers Stevenson Yagi PLLC; Matthew Compton

(57) ABSTRACT

A sensor system useable in conjunction with one or more environmental fixtures is disclosed. Each of the fixtures preferably includes illumination functionality as well as UV sterilization functionality provided by a fan and UV LED chips in the fixture. One of the fixtures is preferably programmed as a master which executes a control algorithm to control and/or monitor the system. The sensor module includes a plurality of sensors for sensing different environmental conditions where the system is utilized. These sensed conditions are provided to the master fixture, whose control algorithm can use the sensed conditions to control one or more functions in each of the fixtures, such as illumination, UV sterilization, and/or fan speed. The master fixture can output necessary controls to other secondary fixtures in the environment. The system may further communicate with or include external devices that can wirelessly communicate with the system using an application.

22 Claims, 15 Drawing Sheets

(56) References Cited

U.S. PATENT DOCUMENTS

| | | | |
|---|---|---|---|
| 6,791,259 B1 | 9/2004 | Stokes et al. | |
| 7,658,891 B1 | 2/2010 | Barnes | |
| 8,074,397 B2 | 12/2011 | Yoneda | |
| 8,297,782 B2 | 10/2012 | Bafetti | |
| 8,302,346 B2 | 11/2012 | Hunt et al. | |
| 8,398,264 B2 | 3/2013 | Anderson | |
| 8,453,376 B2 | 6/2013 | Chen | |
| 8,476,844 B2 | 7/2013 | Hancock et al. | |
| 8,508,204 B2 | 8/2013 | Deurenbeg et al. | |
| 9,039,966 B2 | 5/2015 | Anderson et al. | |
| 9,046,227 B2 | 6/2015 | Aurelien | |
| 9,145,590 B2 | 9/2015 | Evans et al. | |
| 9,162,077 B2 | 10/2015 | Nigola et al. | |
| 9,333,274 B2 | 5/2016 | Peterson | |
| 9,368,695 B2 | 6/2016 | Aurelien | |
| 9,439,989 B2 | 9/2016 | Lalicki | |
| 9,581,310 B2 | 2/2017 | Wu et al. | |
| 9,681,515 B2 | 6/2017 | Rantala | |
| 9,750,105 B2 | 8/2017 | Rantala | |
| 10,104,740 B2 | 10/2018 | Rantala | |
| 10,393,357 B2 * | 8/2019 | Niemiec | F21S 8/061 |
| 10,398,000 B2 | 8/2019 | Rantala | |
| 10,440,900 B1 | 10/2019 | Higgins | |
| 10,509,377 B2 * | 12/2019 | Willette | F24F 11/77 |
| 2003/0124023 A1 | 7/2003 | Burgess et al. | |
| 2004/0008523 A1 | 1/2004 | Butler | |
| 2005/0055070 A1 | 3/2005 | Jones et al. | |
| 2005/0207159 A1 | 9/2005 | Maxik | |
| 2006/0022582 A1 | 2/2006 | Radkov | |
| 2006/0071589 A1 | 4/2006 | Radkov | |
| 2006/0186377 A1 | 8/2006 | Takahashi et al. | |
| 2006/0261742 A1 | 11/2006 | Ng et al. | |
| 2006/0262545 A1 | 11/2006 | Piepgras et al. | |
| 2006/0284199 A1 | 12/2006 | Matheson | |
| 2008/0008620 A1 | 1/2008 | Alexiadis | |
| 2008/0245788 A1 | 10/2008 | Choong et al. | |
| 2008/0278927 A1 | 11/2008 | Li et al. | |
| 2008/0305004 A1 | 12/2008 | Anderson et al. | |
| 2008/0315217 A1 | 12/2008 | Van Der Wel | |
| 2009/0018621 A1 | 1/2009 | Vogler et al. | |
| 2009/0034236 A1 | 2/2009 | Reuben | |
| 2009/0231832 A1 | 9/2009 | Zukauskas et al. | |
| 2009/0267484 A1 | 10/2009 | Kasakura et al. | |
| 2010/0001648 A1 | 1/2010 | De Clercq et al. | |
| 2010/0121420 A1 | 5/2010 | Fiset et al. | |
| 2010/0232135 A1 | 9/2010 | Munehiro et al. | |
| 2010/0244724 A1 | 9/2010 | Jacobs et al. | |
| 2010/0246169 A1 | 9/2010 | Anderson et al. | |
| 2012/0068615 A1 | 3/2012 | Duong et al. | |
| 2012/0099303 A1 | 4/2012 | Li et al. | |
| 2012/0281408 A1 | 11/2012 | Owen et al. | |
| 2012/0286304 A1 | 11/2012 | LeToquin et al. | |
| 2012/0320607 A1 | 12/2012 | Kinomoto et al. | |
| 2013/0077299 A1 | 3/2013 | Hussell et al. | |
| 2013/0139437 A1 | 6/2013 | Maxik | |
| 2013/0194795 A1 | 8/2013 | Onaka | |
| 2013/0313516 A1 | 11/2013 | David et al. | |
| 2013/0313546 A1 | 11/2013 | Yu | |
| 2013/0318869 A1 | 12/2013 | Aikala | |
| 2013/0320299 A1 | 12/2013 | Li | |
| 2014/0034991 A1 | 2/2014 | McKenzie et al. | |
| 2014/0152194 A1 | 6/2014 | Beyer | |
| 2014/0254131 A1 | 9/2014 | Osinski et al. | |
| 2014/0328046 A1 | 11/2014 | Aanegola et al. | |
| 2015/0014715 A1 | 1/2015 | Hsing Chen et al. | |
| 2015/0049459 A1 | 2/2015 | Peeters et al. | |
| 2015/0083221 A1 | 3/2015 | Boonekamp et al. | |
| 2015/0129781 A1 | 5/2015 | Kretschmann | |
| 2015/0182646 A1 | 7/2015 | Anderson et al. | |
| 2015/0196002 A1 | 7/2015 | Friesth | |
| 2015/0342125 A1 | 12/2015 | Krijn et al. | |
| 2016/0015840 A1 | 1/2016 | Gordon | |
| 2016/0030610 A1 | 2/2016 | Peterson et al. | |
| 2016/0088802 A1 | 3/2016 | Nicole et al. | |
| 2016/0249810 A1 | 9/2016 | Darty et al. | |
| 2016/0271281 A1 | 9/2016 | Clynne et al. | |
| 2016/0273717 A1 | 9/2016 | Krames et al. | |
| 2016/0276550 A1 | 9/2016 | David et al. | |
| 2016/0296649 A1 * | 10/2016 | Ramanand | A61L 2/10 |
| 2016/0375161 A1 | 12/2016 | Hawkins et al. | |
| 2016/0375162 A1 | 12/2016 | Marry et al. | |
| 2016/0375163 A1 | 12/2016 | Hawkins et al. | |
| 2017/0014538 A1 | 1/2017 | Rantala | |
| 2018/0119973 A1 | 5/2018 | Rothman et al. | |
| 2018/0147417 A1 | 5/2018 | Rantala | |
| 2018/0224093 A1 | 8/2018 | Dutta et al. | |
| 2019/0113219 A1 | 4/2019 | Niemiec et al. | |
| 2019/0292315 A1 | 9/2019 | Niemiec et al. | |
| 2019/0388903 A1 * | 12/2019 | Vossoughi Khazaei | H05H 1/4645 |
| 2020/0009286 A1 * | 1/2020 | Zarcone | H05B 47/19 |
| 2020/0038542 A1 * | 2/2020 | Franklin | H01L 25/0753 |
| 2021/0010701 A1 * | 1/2021 | Nesler | F24F 3/14 |
| 2021/0393834 A1 * | 12/2021 | Wellig | F24F 11/63 |

FOREIGN PATENT DOCUMENTS

| | | | | |
|---|---|---|---|---|
| CN | 103947469 | | 7/2014 | |
| CN | 103947470 | | 7/2014 | |
| CN | 104056289 | | 9/2014 | |
| CN | 205434435 U | * | 8/2016 | |
| CN | 112172476 | | 1/2021 | |
| EP | 2554583 | | 2/2013 | |
| JP | S6420034 | | 1/1989 | |
| JP | 2003339845 | | 12/2003 | |
| KR | 1020130125436 | | 11/2013 | |
| KR | 20170036435 A | * | 4/2017 | A61L 2/10 |
| KR | 1020170114678 | | 10/2017 | |
| KR | 101803267 | | 12/2017 | |
| KR | 102042655 | | 11/2019 | |
| WO | 2001/014012 | | 3/2001 | |
| WO | 2002/067660 | | 9/2002 | |
| WO | 2003/063902 | | 8/2003 | |
| WO | 2004/033028 | | 4/2004 | |
| WO | 2006/100303 | | 9/2006 | |
| WO | 2006/126482 | | 11/2006 | |
| WO | 2007/012875 | | 2/2007 | |
| WO | 2007/049180 | | 5/2007 | |
| WO | 2009/045107 | | 4/2009 | |
| WO | 2009/056838 | | 5/2009 | |
| WO | 2013/141824 | | 9/2013 | |
| WO | 2014/188303 | | 11/2014 | |
| WO | 2015/066099 | | 5/2015 | |
| WO | 2016/019029 | | 2/2016 | |
| WO | 2016/081959 | | 5/2016 | |

OTHER PUBLICATIONS

Beelmann et al., "Post-harvest Vitamin D Enrichment of Fresh Mushrooms," HAL Project # MU07018, Apr. 30, 2009, Penn State University.

Carvalho et al., "Sequential Light Programs Shape Kale (*Brassica napus*) Sprout Appearance and Alter Metabolic and Nutrient Content," Horticulture Research 1, Article No. 8, 2014.

Eytan et al., "Changes in Photosystem I Activity and Membrane Organization During Degreening and Greening of a Chlamydomon as Reinhardi Mutant, y-1," The Journal of Biological Chemistry, vol. 249, No. 3, Issue of Feb. 10, , p. 738-744, 1974.

Kleuter et al., "Photosynthesis in Cucumbers with Pulsed or Continuous Light," Transactions of the ASABE, 23(2): 0437-0442, 1980.

Lefsrud et al., "Irradiance from Distinct Wavelength Light-Emitting Diodes Affect Secondary Metabolites in Kale," HortScience, vol. 43, No. 7, pp. 2243-2244, 2008.

Nicklisch, Andreas, "Growth and Light Absorption of Some Planktonic Cyanobacteria, Diatoms and Chlorophyceae Under Stimulated Natural Light Fluctuations," Journal of Plankton Research, vol. 20, Issue 1, pp. 105-119, 1998.

Olle et al., "The Effects of Light-Emitting Diode Lighting on Greenhouse Plant Growth and Quality," Agricultural and Food Science, vol. 22, No. 2, pp. 223-234, 2013.

(56) References Cited

OTHER PUBLICATIONS

Sforza et al., "Adjusted Light and Dark Cycles Can Optimize Photosynthetic Efficiency in Algae Growing in Photobioreactors," PLos ONE, 7(6): e38975, 2012.

Tennessen et al. "Efficiency of Photosynthesis in Continuous and Pulsed Light Emitting Diode Irradiation," Photosynthesis Research, 44(3), pp. 261-269, 1995.

Vänninen et al. "Prospecting the Use of Artificial Lighting for Integrated Pest Management," ISHS Acta Horticulturae, 956, pp. 593-608, 2010.

Yeh et al., "High-Brightness LEDs—Energy Efficient Lighting Sources and their Potential in Indoor Plant Cultivation," Renewable and Sustainable Energy Reviews, vol. 13, Issue 8, pp. 2175-2180, 2009.

R.M. Tomb et al., "New Proof-of-Concept in Viral Inactivation: Virucidal Efficacy of 405 nm Light Against Feline Calicivirus as a Model for Norovirus Decontamination," Food & Environmental Virology, vol. 9(2), 23 pages (2017).

A.J. DeLucca et al., "Blue Light (470 nm) Effectively Inhibits Bacterial and Fungal Growth," Letters in Applied Biology, vol. 55., pp. 460-466 (2012).

C.D. Ltyle et al., "Predicted Inactivation of Viruses of Relevance to Biodefense by Solar Radiation," J. Virology (vol. 79 (22), pp. 14244-14252 (2005).

K. Bergmann, "UV-C Irradiation: A New Viral Inactivation Method for Biopharmaceuticals," America Pharmaceutical Review, vol. 17(6) (Nov. 2014).

Pinter, Matt, et al., "IEC/EN 62471 (Eye Safety) for LED Lighting Products—Standards for Eye and Skin Safety," Smart Vision Lights, 2009, 4 pages.

Neumark, et al., "Wide Bandgap Light Emitting Materials and Devices," John Wiley & Sons, 2008, 50 pages.

Dai, Tianhong, et al., "Blue Light for Infectious Diseases: Propionibacterium Acnes, Helicobacter Pylori, and Beyond?" National Institutes of Health—Drug Resist Update, Aug. 2012, 15(4), pp. 223-236.

Daicho, Hisayoshi, et al., "A Novel Phosphor for Glareless White Light-Emitting Diodes," Nature Communications, 3:1132, Oct. 16, 2012, 8 pages.

Setlur, Anant A., "Phosphors for LED-based Solid-State Lighting," The Electrochemical Society Interface, Winter 2009, 5 pages.

TRI-R Project Brochure, Toshiba Materials Co., LTD., retrieved on Aug. 18, 2017, 16 pages.

Partial Search Report regarding corresponding European Application No. 22165405.6, mailed Oct. 11, 2022.

* cited by examiner

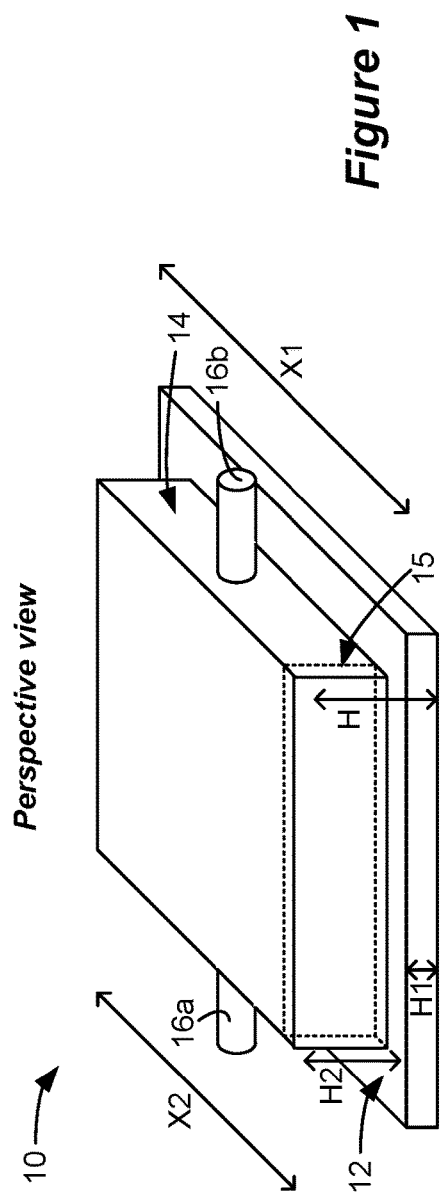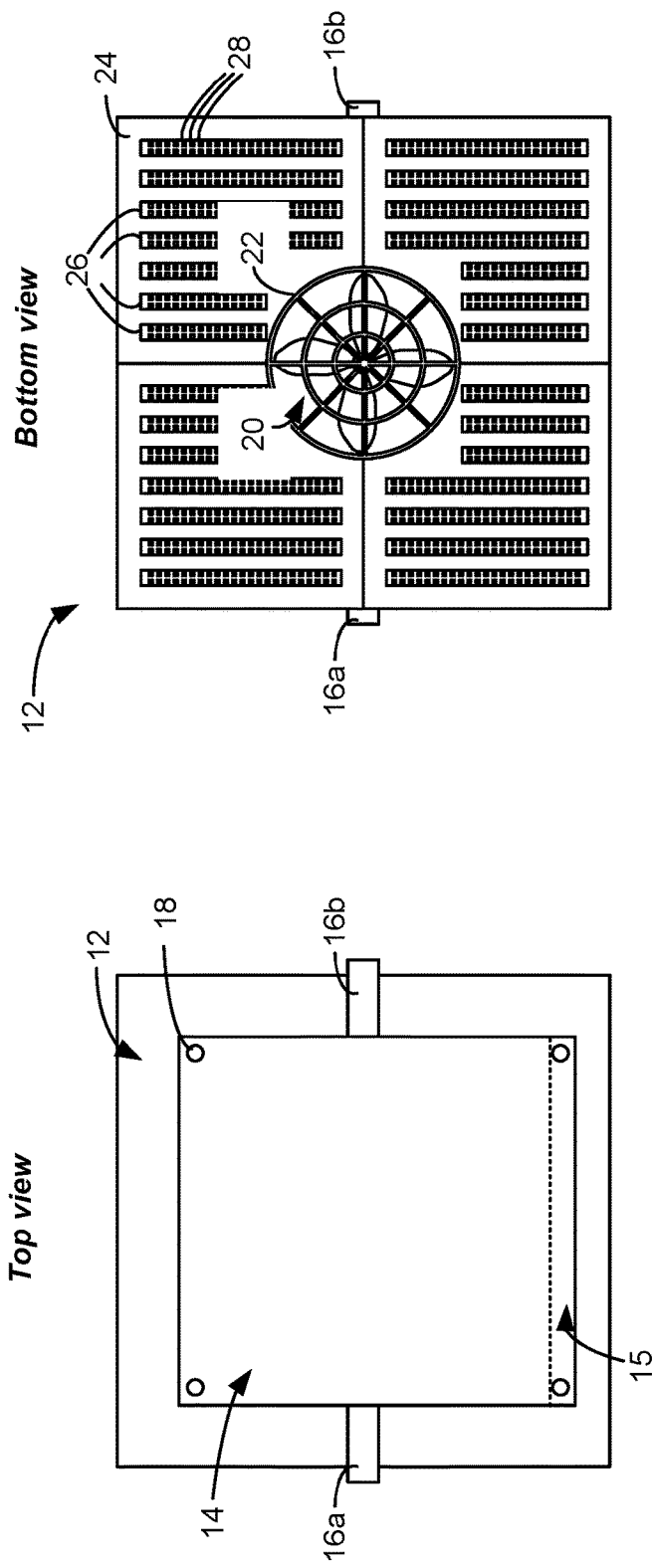
*Figure 1*

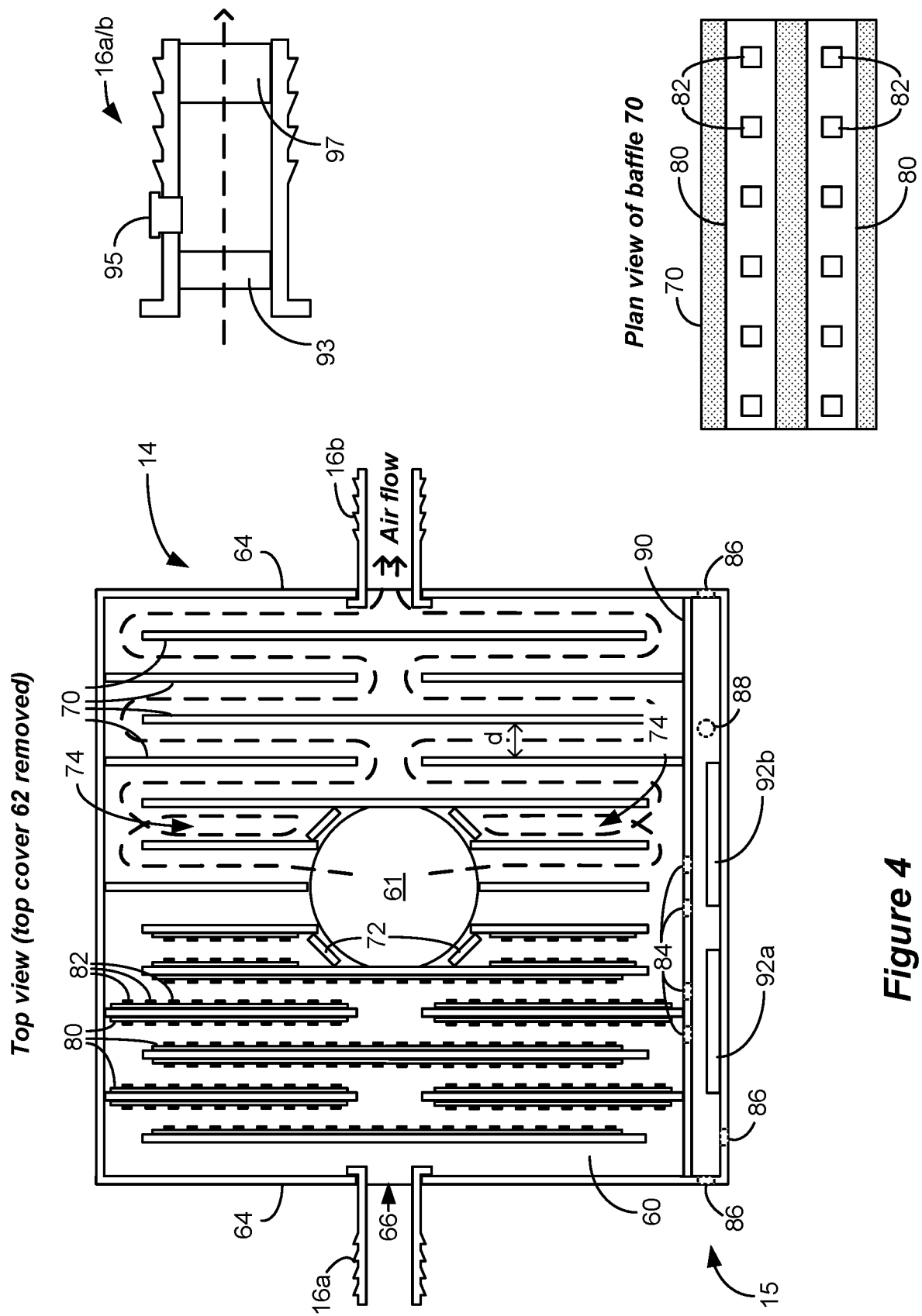

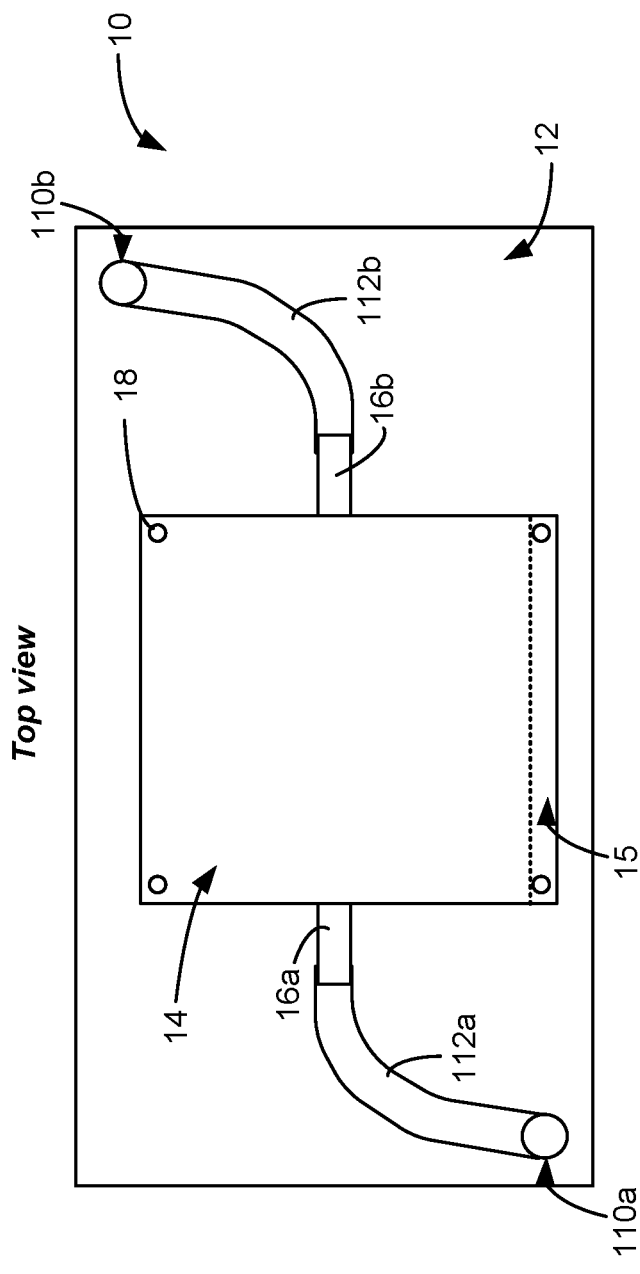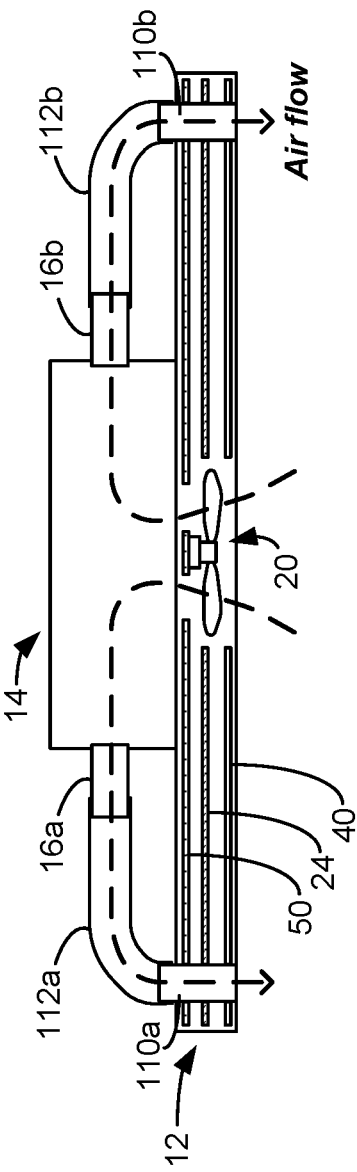
Figure 6A

SENSOR SYSTEM FOR A LIGHT FIXTURE HAVING ULTRAVIOLET STERILIZATION FUNCTIONALITY

CROSS REFERENCE TO RELATED APPLICATIONS

This is a continuation of U.S. Non-Provisional patent application Ser. No. 17/317,656, filed May 11, 2021, to which priority is claimed, and which is incorporated herein by reference.

FIELD OF THE INVENTION

This application relates to a lighting fixture having the ability to sterilize pathogens such as bacteria, fungi, and viruses.

INTRODUCTION

Lighting fixtures are common in commercial buildings and homes. For example, fluorescent bulb fixtures have been used in commercial buildings and homes for years. Over the last decade or so, Light Emitting Diode (LED) based lighting fixtures have been developed which generally have the same size, shape, and mounting hardware as do traditional fluorescent bulb fixtures (typically 2×2 feet or 2×4 feet). This allows older fluorescent bulb fixtures to be easily replaced by LED based fixtures, which is beneficial because LED fixtures are more energy efficient, more reliable, and easier to maintain when compared with fluorescent fixtures.

Another benefit of LED fixtures is that they can provide radiation suitable to provide disinfection as well as providing visual white light. For example, U.S. Patent Application Publication 2018/0147417 discloses a LED chip useable in a lighting fixture. The LED chip includes a first LED that emits light at 405 nm in the near ultraviolet (UV) range. (The wavelength of light in the visible spectrum ranges from 380 nm at the UV end of the spectrum to 740 nm at the infrared (IR) end of the spectrum). The LED chip also includes a second LED that emits at 450 nm in the blue range of visible light. The LEDs in the chip are coated by a phosphor material, and for the most part the 405 nm radiation passes through the phosphor without absorption. The 450 nm radiation by contrast interacts with the phosphor where it is converted to higher wavelengths, which results in a broader white light emission spectrum. In sum, the LED chip produces an overall spectrum with a peak at 405 nm, as well as a broader-wavelength white spectrum. The inclusion of a significant amount of 405 nm light in the overall spectrum is beneficial, because radiation at that wavelength is known to disrupt certain microbial biological processes. For example, the '417 Publication explains that 405 nm radiation causes reactive oxygen species generation in cells, which in turn prevent cell metabolism and effectively suppresses bacterial growth. 405 nm radiation has also been reported as providing disinfection against fungi. See R. M. Tomb et al., "New Proof-of-Concept in Viral Inactivation: Virucidal Efficacy of 405 nm Light Against Feline Calicivirus as a Model for Norovirus Decontamination," Food & Environmental Virology, Vol. 9(2), pp. 159-67 (2017).

While LED fixture having disinfection properties such as those just described are beneficial, the inventor sees room for improvement. For one, other wavelengths—such as 470 nm—have also been shown to have antibacterial as well as antifungal properties. See, e.g., A. J. DeLucca et al., "Blue Light (470 nm) Effectively Inhibits Bacterial and Fungal Growth," Letters in Applied Biology, Vol 55., pp. 460-66 (2012). But wavelengths such as 405 nm and 470 nm may not be effective against viruses. The article by R. M. Tomb, cited above, investigates the use of 405 nm radiation to inactivate viruses, and while promising results were shown, it appears that much higher doses of 405 nm radiation may be necessary to provide viral disinfection. As 405 nm radiation may be irritating to human eyes, see '417 Publication, it may not be useful to increase the intensity of 405 nm radiation in an otherwise white-light LED fixture in the hopes that it will also kill viruses.

Furthermore, the flux or energy density of pathogen-inactivating radiation, such as at 405 and 470 nm, provided by a light fixture may not be sufficient to inactivate air borne pathogens. In short, the volume of the room in which a light fixture is placed may be too large to effectively inactivate air borne pathogens.

The inventor discloses a comprehensive solution in the form of a white light LED fixture with effective disinfection properties against bacteria, fungi, and viruses. As discussed further below, the white light LED fixture includes a fan to continuously draw air into the light fixture. The air drawn in is irradiated with UV radiation within the fixture, such as is provided from UV LED chips. The relatively small volume of the light fixture allows the flux or energy density of the UV radiation to be made more intense. After the air is sterilized, it can be put back into the room or building in which the fixture is placed. The white light provided by white light LEDs in the fixture provides illumination, and can further provide significant emission peaks at 405 nm and 470 nm which is also useful to pathogen inactivation.

BRIEF DESCRIPTION OF THE DRAWINGS

FIG. 1 shows various views of an improved lighting fixture, having a light box, a fan to draw in air, and a UV sterilization box through which the drawn air passes.

FIG. 4 shows a top down view of the UV sterilization box with its cover removed, including UV LED chips and baffles to define a non-linear path for the air drawn into the fixture by the fan.

FIG. 6A shows that sterilized air output from the UV sterilization box can be output back into a room through ports provided in the light box.

DETAILED DESCRIPTION

Figure 2B:
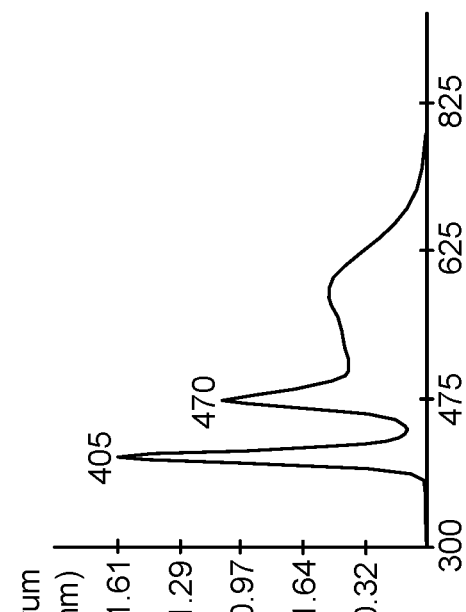
FIGS. 2A and 2B show white LED chips that can be used in the light box, which preferably produce a white light spectrum having significant near-UV peak wavelengths at 405 and 470 nm, which have shown to be useful to inactivate bacteria and fungi.

An example of a disinfecting light fixture 10 is shown in FIG. 1 in perspective, top down, and bottom up views. The fixture 10 has two main sections: a light box 12, and a UV sterilization box 14. Note that these "boxes" 12 and 14 do not need to be box-shaped as shown, and boxes 12 and 14 can instead be understood as any compartment, region, or volume in the fixture 10 however shaped and sized.

The light box 12 includes white LED chips 28 which provide for illumination and whose spectrum additionally and preferably includes significant radiation at 405 nm and 470 nm, as explained further below. The light box 12 includes a fan 20 protected by a grate 22. The fan 20 is used to draw air into the UV sterilization box 14 where the air is disinfected with UV radiation provided by UV LED chips 82 (FIG. 4), again discussed further below. One or more holes 66 (FIG. 3A) are present in the UV sterilization box 14, and hose connectors 16*a* and 16*b* can be fitted in these holes. The air drawn into the UV sterilization box 14 by the fan 20 exits the fixture 10 through these hose connectors 16*a* and 16, thus outputting sterilized air.

Notice then that the disinfecting light fixture 10 includes different means of providing sterilization of pathogens. The white LED chips 28, as well as providing white light for illumination, include significant radiation at 405 and 470 nm, which are useful in inactivating at least bacteria and fungi in the air and on surfaces in the room being illuminated, as discussed above. Other air borne pathogens—in particular viruses—are drawn into the fixture by the fan 20 and subjected to high intensity UV radiation provided by the UV LED chips 82 in the UV sterilization box 14. Such UV radiation should inactivate such air borne viruses, see C. D. Lytle et al., "Predicted Inactivation of Viruses of Relevance to Biodefen se by Solar Radiation," J. Virology (Vol. 79 (22), pp. 14244-52 (2005), and would be expected to provide further sterilization of other air borne pathogens (bacteria and fungi) as well. The air as sterilized by the fixture 10 can then be put back into the room where the fixture 10 is located, or otherwise may be input into the air handling system of the building, as explained further below. Notice that the fixture 10's sterilization properties makes it particularly well suited for use in locations where pathogens can be problematic, such as hospitals, nursing homes, etc. Fixture 10 is also useful when incorporated into grow light systems use to grow plants, such as in the system described in U.S. Pat. No. 10,440,900, which is incorporated herein by reference in its entirety. Sterilization is important in this context as well, because growing plants are susceptible to pathogens such as viruses, bacteria, and fungi.

FIG. 1 shows an example of a 2×2 feet (X1) fixture 10, although the fixture could be made of any shape and size. The UV sterilization box 14 may be smaller in area, e.g., approximately 1.5×1.5 feet (X2). The total height H of the fixture 10 is preferably about six inches, with the light box 12 having a height of about 1.5 inches (H1) and the UV sterilization box 14 having a height of about 4.5 inches (H2). These dimensions are merely one example, and both the light box 12 and the UV sterilization box 14 can have other dimensions as well. The fixture 10 so sized comprises a suitable replacement for traditional fluorescent bulb fixtures. Means for mounting the fixture 10 (e.g., to a room's ceiling) are not shown, but can be of conventional design.

The top view shows that the UV sterilization box 14 can include a section 15 for necessary system electronics, as described later. The bottom view shows the underside of the fixture 10 that which would provide illumination into the room. The fixture 10's diffuser 40 (FIGS. 3A and 3B) is removed for easier viewing of underlying structures. Visible from this view are one or more circuit boards 24 which support LED strips 26. Each LED strip 26 includes a number of white LED chips 28, which are described in detail with respect to FIGS. 2A and 2B. The size, number, and location of the LED strips 26 is variable, as are the number, type, and location of the white LEDs chips 28 on these strips. In the example shown, there are four circuit boards 24, each being approximately 1×1 foot, although a single circuit board 24 could be used as well. Although not yet shown in the figures, the circuit board(s) include a hole 25 to accommodate the fan 20.

Figure 2A:
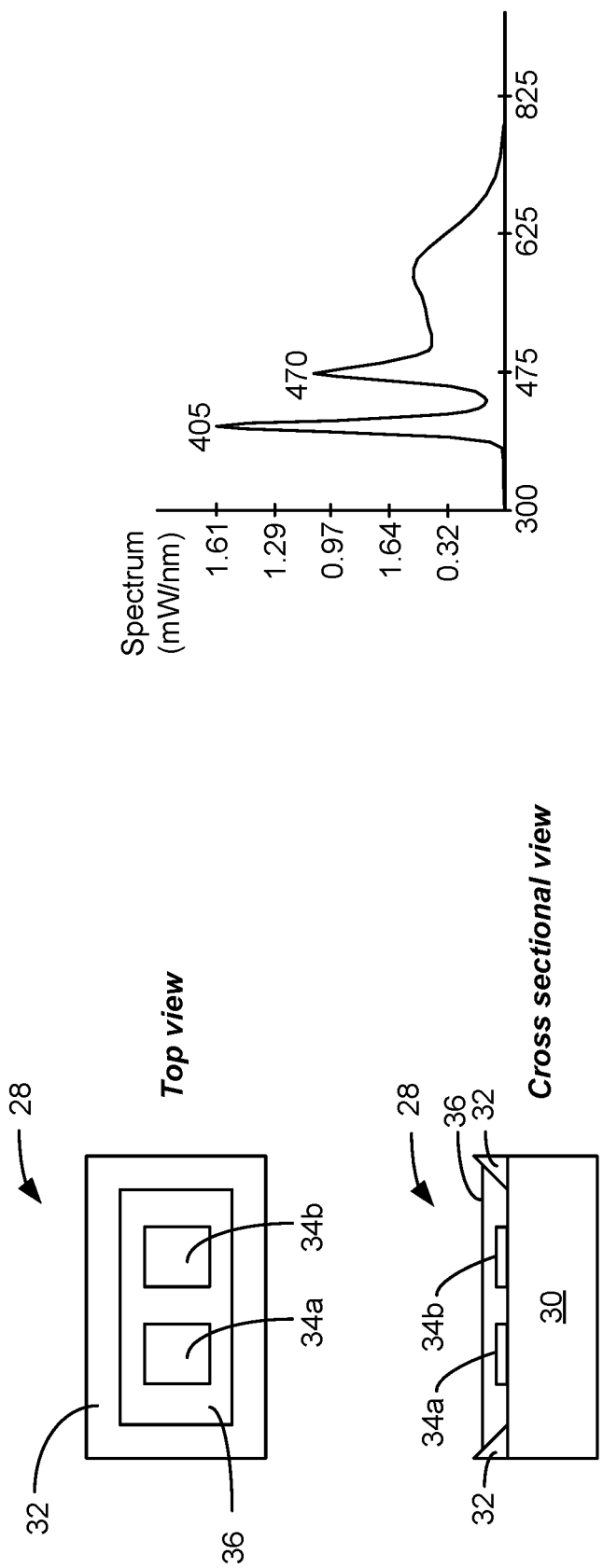

FIG. 2A shows an example of the white LED chip 28, while FIG. 2B shows the spectrum that results from use of this chip. A white LED chip 28 is shown in top down and cross sectional views, and includes two LEDs 34*a* and 34*b* mounted to a substrate 30. A cavity wall 32 surrounds the LEDs 34*s* and 34*b* and helps to direct light out of the chip 28. Preferably, the LEDs 34*a* and 34*b* are different, and emit at different peak wavelengths. For example, LED 34*a* can emit at a peak wavelength of 405 nm, while LED 34*b* can emit at a peak wavelength of 470 nm. In this example, the LEDs 34*a* and 34*b* are covered with a phosphor 36. The phosphor 36, as one skilled in the art will appreciate, can comprise a mixture of different photosensitive chemicals. Although electrical connections to the LEDs 34*a* and 34*b* within the chip 28 are not shown, the LEDs can be driven with a current in series or in parallel, or each can be independently driven by their own currents. Each of the LEDs 34*a* and 34*b* could also be covered with their own unique phosphors as well, or covered with no phosphor at all, although this isn't shown.

As shown in the emission spectrum of the white LED chip 28 in FIG. 2B, it is assumed that the 405 nm radiation largely breaks through the phosphor 36 without being absorbed, and thus this radiation does not substantially contribute to the production of longer wavelengths which would broaden the spectrum. Thus, the spectrum shows a sharp leak at 405 nm. The 470 nm radiation by contrast is designed to interact with the phosphor 36 to produce longer wavelengths, which broadens the spectrum from about 470 to 775 nm, which in sum produces white light useful for illumination. Some amount of the 470 nm radiation is not absorbed by the phosphor 36, and thus the spectrum includes another peak at this wavelength. Thus, the overall spectrum thus has significant high intensity peaks at 405 nm and 470 nm, but also a broad spectrum that in sum produces white light. In short, the white LED chips 28 in the light box 12 produce white light having significant intensities at 405 and 470 nm. As noted above, inclusion of these peak wavelengths is preferred in the disinfecting light fixture 10 because such radiation impedes (at least) bacterial and fungal growth. One skilled in the art will understand that the disinfection benefits provided by the LEDs 34*a* and 34*b* are still had even if the peak wavelengths produced by those LEDs are not exactly at 405 nm and 470 nm. In this regard, the LEDs 34*a* and 34*b* may produce radiation at approximately 405 nm and/or 470 nm, where approximately means a wavelengths that is plus or minus 10 nm from these ideal wavelengths— i.e., from 395 nm 415 nm (in the case of the 405 nm LED 34*a*), and from 460 nm to 480 nm (in the case of the 470 nm LED 34*b*).

Figure 3A:
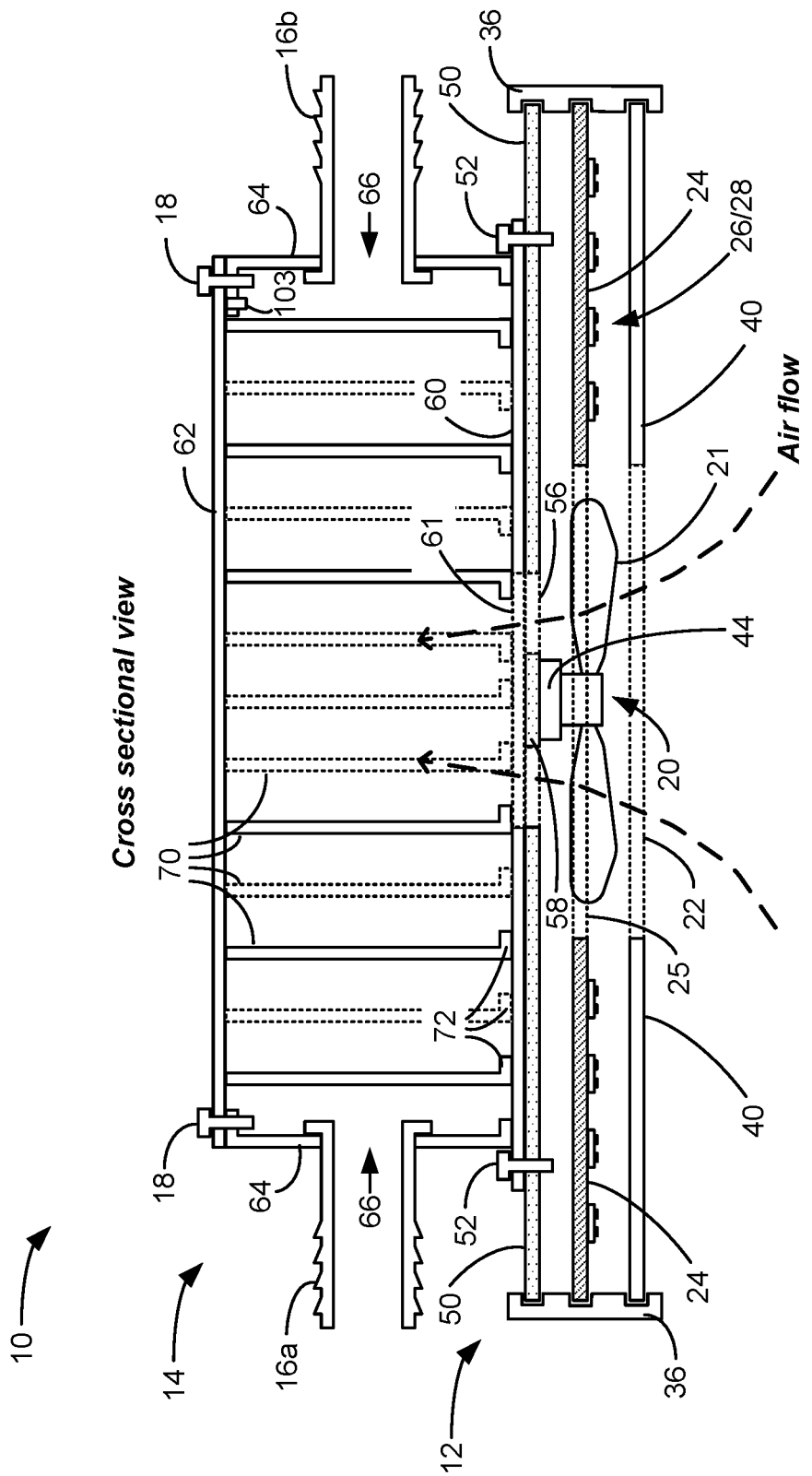
FIG. 3A shows a cross section of the lighting fixture.
Figure 3B:
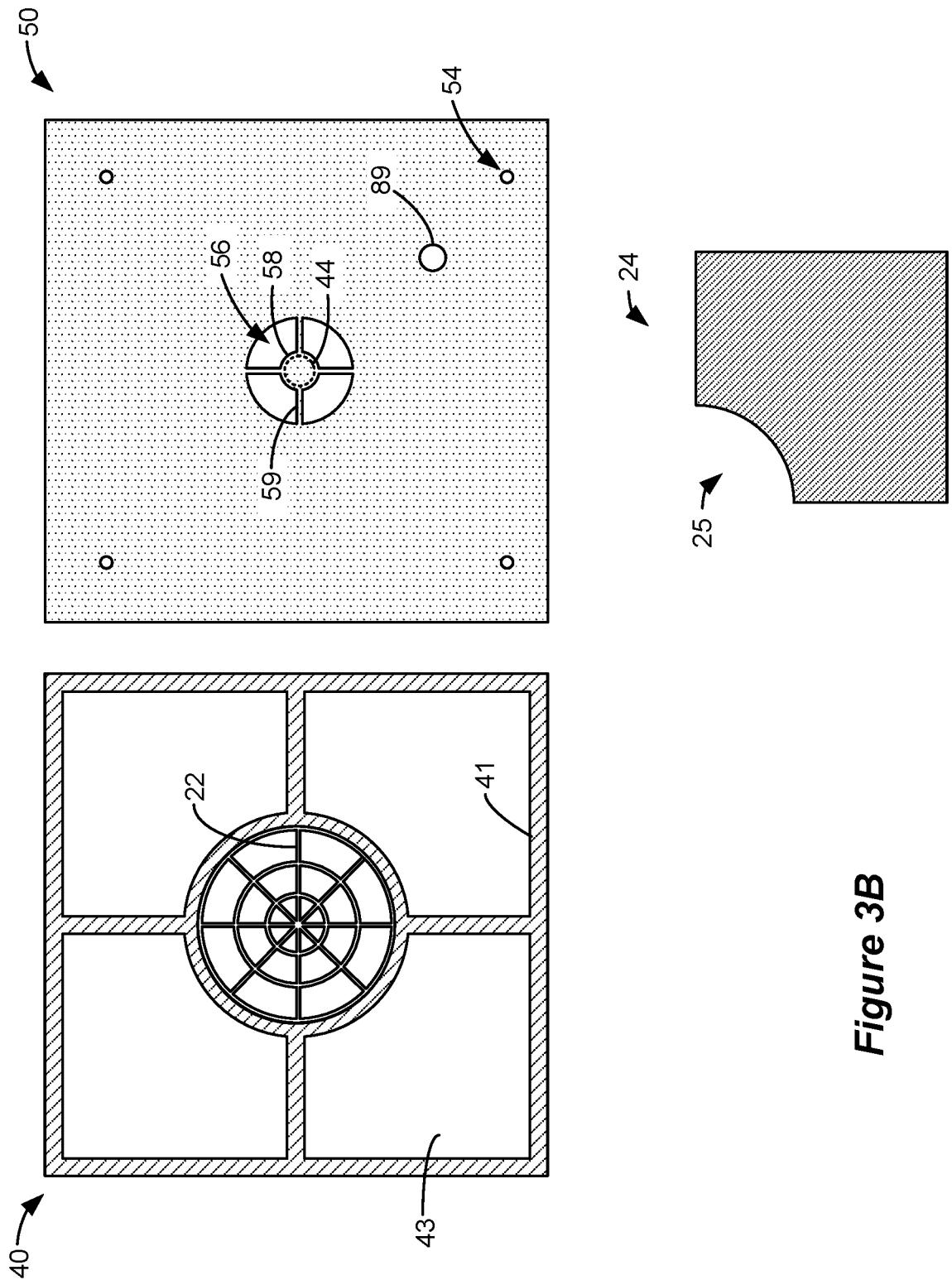
FIG. 3B shows the fixture's back plane, diffuser, and one of its circuit boards of the light box.

Further sterilization—in particular, of viruses—is provided by the UV sterilization box 14, although before discussing such details, the construction of the light fixture 10 is described, starting with FIGS. 3A and 3B. The light box 12 includes a diffuser 40, one or more circuit board sections 24 containing the LED strips 26 as already described, and a back plane 50. The diffuser 40, the circuit board(s) 24, and the back plane 50 are essentially formed in parallel planes inside the light box 12, and are held in place using a frame 36. This method of construction is described in U.S. Pat. No. 10,440,900, which was incorporated above. As explained in the '900 patent, the frame 36 can comprise four panels (for each of the four edges of the light box 12). These panels of frame 36 can be positioned around the diffuser 40, the circuit board(s) 24, and the back plane 50, and then connected to hold these structures securely in place.

The diffuser 40 is positioned between the white LED chips 28 and the room to be illuminated, and is shown in further detail in FIG. 3B. The diffuser 40 operates to scatter light produced by the white LED chips 28 to produce a combined emission spectrum (from white LED chips 28; FIGS. 2A and 2B) in the illuminated room that is more spatially homogenous. Preferably, the diffuser 40 includes a lens material 43 that is substantially transparent to the emission spectrum that the white LED chips 28 produce. The lens material 43 is typically made of various glass or plastic materials, such as a polycarbonate light-diffusing white material, and preferably allows good transmittivity of radiation at 405 and 470 nm in particular. The diffuser 40 can further include a brace 41, preferably made of a metallic material. The brace 41 acts to hold the lens material 43 and the fan grate 22, as well as providing a decorative element to the fixture 10. As shown, in this example, the brace 41 divides the diffuser 40 into quarters, and thus the lens material 43 may similarly be formed in quartered segments. Notice that the lens material 43 does not block the fan grate 22, and thus there is a hole in the lens material to allow for air flow into the light box 12 as promoted by operation of the fan 20. Note that the fan grate 22 need not be connected to the diffuser 40. In another example, the fan grate 22 can be connected to the fan 20 or to other structures in the light box 12, with the fan grate 22 then positioned in the hole in the diffuser 40 during construction.

FIGS. 3A and 3B also show details of the back plane 50. The back plane 50 is preferably formed of a single sheet of a metallic material such as steel or aluminum. The back plane 50 preferably includes a landing 58 to which the motor 44 of the fan 20 can be mounted. As best seen in FIG. 3B, the landing 58 is connected to the bulk of the back plane 50 via straps 59, thus defining holes 56 around the periphery of the landing 58. These holes 56 allow air flow to pass from the light box 12 into the UV sterilization box 14, as described subsequently. Port 89 in the back plane 50 allows for system signaling to be passed from the UV sterilization box 14 to the electronics on circuit board(s) 24 and to the fan 20, as discussed later.

As noted, the circuit board 24 can be formed in segments, and FIG. 3B shows one such segment. Notice that the circuit board segment 24 includes a cut out 25, which defines a hole when all circuit board segments are positioned in place in the fixture 10. Again, this hole 25 allows for air flow produced by the fan 20. Although such details aren't shown, the circuit board(s) 24 are preferably affixed to the back plane 50, and this can occur in different ways. The circuit board(s) 24 can be screwed to the back plane 50, possibly using stand offs which provide an air gap between the circuit board(s) 24 and the back plane 50. Alternatively, and to promote heat conduction away from the circuit board(s) 24, the circuit board (s) 24 can be affixed in good thermal contact with the back plane 50 using heat conductive tape, paste, or epoxy for example. Although not shows, the outside of the back plane 50 can include heat sinks, as explained in the above-incorporated '900 patent. Note that a benefit of incorporating fan 20 into the light box section 12 is that it promotes heat transfer away from the circuit board(s) 24, as well as air sterilization functionality.

To summarize, when the fan 20 is operating, air is drawn through fan grate 22, through the hole 25 in the circuit board(s) 24, and through holes 56 in the back plane 50 and into the UV sterilization box 14, whose construction is discussed next. As best shown in FIG. 3A, the UV sterilization box 14 includes a bottom surface 60, side surfaces 64, and a top cover 62. The inside of the UV sterilization box 14 includes baffles 70 which direct the air flow in a non-linear path and ultimately to holes 66 formed in the side surfaces 64. As noted earlier, hose connectors 16*a* and 16*b* are connected to these holes 66. As will be explained in further detail later, these baffles 70 include UV LED chips 82 to irradiate the air flow as it follows this non-linear path, which is described subsequently with respect to FIG. 4. The baffles 70 preferably comprise a metallic material, and are preferably affixed to the bottom surface 60. For example, the bottom edges of the baffles 70 can be bent 72 and affixed to the bottom surface 60 by spot welding, the use or screws, or the use of adhesives. The side surfaces 64 may be similarly attached to the bottom surface 60. In another example not shown, the baffles 70 may be integrated as a single piece, which can then be dropped into the UV sterilization box 14 during its assembly and affixed in place as necessary.

Components of the fixture 10 may be coated with antimicrobial or reflective materials. For example, the interior surfaces of the UV sterilization box 14 may be coated with Titanium Dioxide. As well as having antimicrobial properties, Titanium Dioxide is highly reflective, thus encouraging reflection of the UV radiation within the UV sterilization box 14. This is preferred to absorption of the UV radiation, because absorption removes useful energy that could otherwise be used for disinfection of pathogens. In one example, the coating can comprise Paint Shield®, manufactured by Sherwin Williams. Such a coating can be applied to the vertical surfaces of the baffles 70, and could also be applied to the underside of the top cover 62, and the top side of the bottom surface 60.

The top cover 62 is preferably affixed to the side surfaces 64 using screws 18. This allows the top cover 62 to be removed to perform maintenance on the fixture 10, such as to clean or remove the baffles 70 or to repair or replace system electronics, as explained subsequently. The top cover 62 can be affixed to the UV sterilization box 14 using other methods which allow it to be opened and reclosed for maintenance purposes. Although not shown, the hose connectors 16*a* and 16*b* may also connect to one or more holes provided in the top cover 62.

The UV sterilization box 14 preferably includes a safety switch 103 designed to cut power to the UV LED chips 82 when the top cover 26 is removed. This is to prevent accidental UV exposure to persons who may be assembling or maintaining the light fixture 10. This switch 103 can be provided in the UV sterilization box 14 in different ways, but as shown the switch is mounted to the top flange of the side surface 64. As one skilled will understand, switch 103 includes a contact surface that will be depressed by the top cover 62 when it is connected to the UV sterilization box 14, thus closing the switch 103 and enabling the UV LED chips 82 to receive power. When the top cover 62 is removed, the contact surface is not depressed and switch 103 is thus opened to prevent activation of the UV LED chips 82. Operation of the safety switch 103 is discussed further below with reference to FIG. 5A.

The UV sterilization box 14 is preferably fully constructed and then affixed to the light box 12. In the example shown, this occurs using screws 52 which affix the bottom surface 60 of the UV sterilization box 14 to the back plane 50 of the light box 12. However, the UV sterilization box 14 and light box 12 can be affixed using different means. Furthermore, the UV sterilization box 14 and light box 12 need not be separately constructed and then attached to each other. Instead, the fixture 10 may be constructed in a manner that integrates the functionality of the UV sterilization box 14 and the light box 12. Having said this, it can be preferable to manufacture each separately, as this makes it easier to retrofit otherwise standard light boxes 12 with a UV sterilization box 14.

As best seen in FIGS. 3A and 4, the bottom surface 60 of the UV sterilization box 14 has a hole 61 of preferably the same diameter as the hole(s) 56 formed in the back plane 50 of the light box 12, which promotes air flow from the fan 20 into the UV sterilization box 14. Once such air enters the UV sterilization box 14, it is directed through a non-linear path as directed by the positioning of the baffles 70. This is best shown in FIG. 4, which shows a top down view of the UV sterilization box 14 with the top cover 60 removed. As shown, the baffles 70 are positioned such that the air flow largely follows a serpentine path from the hole 61 in the bottom surface 60 to the holes 66 in the side surfaces 64 that meet with the hose connectors 16a and 16b. The particular manner in which the baffles 70 are positioned in FIG. 4 splits the air flow into four paths. Two of these air flow paths are shown to the right in FIG. 4, although it should be understood that two other air flow paths would be present in the left of FIG. 4, although these aren't shown for simplicity. Note that the air flow paths may not follow a strict serpentine path. For example, the baffles 70 can be positioned to create vortices 74 in the air flow paths. This effectively elongates the air flow path, which exposes air to UV radiation for a longer time, as explained further below. Baffles 72 can be positioned so as to close the air flow paths as necessary to form vortices 74, as well as to direct the air flow into the baffle structure. Note that the two air flow paths shown to the right eventually join at hole 66 to which hose connector 16b is affixed. The other two air flow paths on the left join at hole 66 to which hose connector 16a is affixed.

To more completely sterilize the air in the air flow paths, the non-linear air flow path includes UV LED chips 82, which may be formed on LED strips 80. The UV LED chips 82 and strips 80 are shown to the left in FIG. 4, although it should be understood that UV LED chips 82 and strips 80 would also be present in the right of FIG. 4, although this isn't shown for simplicity. In the example shown, the LED strips 80 are affixed to the vertical surfaces of the baffles 70, as shown in the plan view at the bottom right in FIG. 4. In this example, there are two UV LED strips 80 spaced vertically on the walls of the baffles 70, which improves exposure of the air to UV radiation.

Preferably, as much of the non-linear air flow paths are exposed to UV radiation as possible, and so in FIG. 4 the UV LED strips 80 are essentially positioned along the entirety of the lengths of the air flow paths, and further preferably are positioned along at least half of these lengths. The width d of the air flow paths around the baffles 70 can may be approximately 1 to 1.5 inches. Assuming that the UV sterilization box 14 is approximately 1.5×1.5 feet (X2, FIG. 1), the length of each of the four air flow paths is approximately 60 to 100 inches, and thus irradiation preferably occurs for at least approximately 30 to 50 inches along these paths. Because the UV radiation may be harmful to people, it is preferable that the UV LED strips 80 not appear in positions where the UV radiation could shine or leak out of the UV sterilization box 14. Thus, for example, the UV LED strips 80 are not proximate the air input hole 61, nor are they proximate the output holes 66 to which the hose connectors 16a and 16b are affixed. UV LED strips 80 may as shown be placed on both sides of the baffles 70, which irradiates the air flow paths from opposing sides. While it is preferred to place the UV LED strips 80 on the vertical surfaces of the baffles 70, they could be placed elsewhere as well, such as on the top side of the bottom surface 60, or the underside of the top cover 62.

Assuming that the height of the UV sterilization box 14 is about 4.5 inches (H2, FIG. 1), the total volume of each of the four air flow paths is approximately 360 cubic inches. Fan 20 may for example comprise Part No. 09225VA-12K-AA-cc, manufactured by NMB Technologies Corp., which moves air with a flow rate of 54 cubic feet/minute, which would move air through each of the four air flow paths in parallel at a flow rate of 13.5 cubic feet/minute, or 389 cubic inches/second. As such, each unit volume of air in each flow path is constantly UV irradiated for approximately one second (360/389), and with a high flux or energy density because the air is being irradiated almost continuously along the length of each air flow path. Note this is advantageous when compared with other air purification system that use UV radiation to purify air. Typically such systems involve a point UV source which the air to be sterilized rushes passed, meaning that each unit volume of air is only radiated for a short time, which may result in incomplete inactivation of pathogens. By contrast, the air is constantly irradiated in the UV sterilization box 14 along the non-linear paths for an extended period of time, and with a high flux or energy density, thus ensuring more complete disinfection. Of course, the extent to which air is UV irradiated could be varied by changing the flow rate of the fan 20, changing the length or volume of the air flow paths, changing the intensity and number of UV LED chips 82 used, etc.

In one example, each of the UV LED chips 82 on UV LED strips 80 produces UV radiation with a peak wavelength in the range of 200 to 280 nm, which generally corresponds to the range of UV-C wavelengths. More preferably, the UV radiation has a peak wavelength in the range of 240 to 260 nm, or in the range of 260 to 280 nm. UV radiation in this range has been shown to be particularly useful to inactivate viruses by targeting their nucleic acids. See K. Bergmann, "UV-C Irradiation: A New Viral Inactivation Method for Biopharmaceuticals," America Pharmaceutical Review, Vol 17(6) (November 2014).

While FIG. 4 shows four air flow paths each following a non-linear path, and two output holes 66, it should be understood that this is just one example. There could be more or less air flow paths established with the UV sterilization box 14, or more or less holes 66. For example, a single non-linear path could comprise a spiral in which air input via hole 61 spirals around the box 14 at increasing diameters, until the sterilized air eventually exits the box at a single output hole 66.

FIG. 4 shows further options that can be included with the UV sterilization box 14, and in particular with the hose connectors 16a and 16b. As shown in the upper right, the interior diameter of the hose connectors 16a/b includes a one-way valve 93 that only allows sterilized air to pass out of the UV sterilization box 14. The hose connectors 16a/b may also include a pressure relief valve 95 which is designed to vent the sterilized air should it exceed the valve 95's pressure. The interior diameter of the hose connectors 16a/b can also include filters 97, such as charcoal filters, to further filter particulates and pathogens, and to also work as an anti-odorant. The anti-odorant properties of the filter 97 can be particularly useful when the fixture 10 is used in a grow farm setting and when the plants being grown have strong odors (e.g., *cannabis*). The filters and valves need not necessarily be positioned within the hose connectors 16a/16b, but could comprise discrete components connected to the hose connectors 16a/b outside the box 14. Although not shown, the air flow paths within the UV sterilization box 14 could include filters and valves at various points as well.

As shown in FIG. 4, the UV sterilization box 14 can include an electronics section 15. This section 15 can be walled off from the baffles 70 and the air flow paths by a wall 90. Section 15 can include the driver circuitry 92a for driving drive the white LED chips 28 in the light box 12 and driver circuitry 92b for driving the UV LED chips 82 in the UV sterilization box 14. It is preferable that the driver circuits 92a and 92b be separate because the white LED chips 28 and UV LED chips 82 may have different driving requirements (voltages, currents, power, etc.). Driver circuitries 92a and 92b could also be integrated in another example.

Electronics section 15 can include or more ports 86 which receive AC power 100 (FIG. 5) from outside the fixture 10, e.g., from a socket or other power source or line to which the fixture 10 is connected. The section 15 may also include a port 88 in the bottom surface 60 to allow signaling to be output from driver circuitry 92a to the white LED chips 28 in the light box 12. Port 88 can correspond in position to a similar port 89 in the back plane 50 of the light box 12 (see FIG. 3B). Although not shown, one skilled will understand that such signaling will connect to connectors or contacts on one or more of the circuit board(s) 24. AC power for the fan 20 can also pass through the ports 88/89.

Electronics section 15 may also include one or more ports 84 to allow signaling to be output from driver circuitry 92b to the UV LED chips 82 in the UV sterilization box 14 and to the safety switch 103. One skilled will understand that such signaling will connect to each of the UV LED strips 80. In this regard, it can be useful to connect the various UV LED strips 80 within the UV sterilization box in a manner to reduce the amount of signaling and connections required. Although not shown, the bottom surface 60 can include a circuit board to assist in routing signaling to the UV LED strips 80. This circuit board may include, or be in addition to, a circuit board 11 that is used to control the fixture, as explained further later. Preferably, port(s) 84 are optically blocked after the signaling has passed through to prevent UV light from entering electronics section 15. It is preferable to include the system electronics within section 15 so it can be easily accessed. For example, top cover 62 of the UV sterilization box 14 can be removed (using screws 18, FIG. 3A), thus allowing access as necessary to maintain or replace system electronics. System electronics could also be located in the light box 12. The size of electronic section 15 can vary depending on the size of the system electronics that are supported.

Figure 5A:
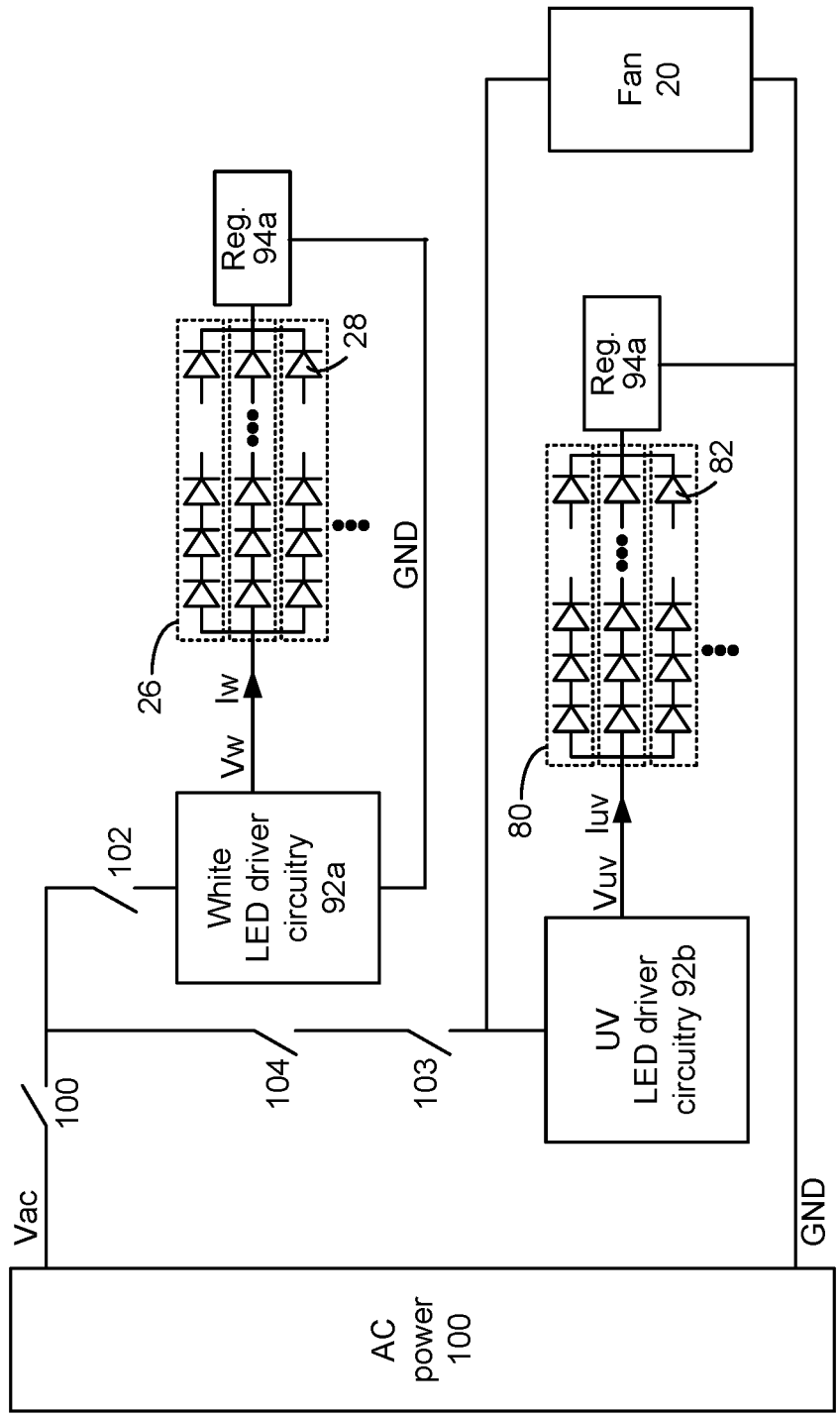
FIGS. 5A and 5B shows the system electronics for the fixture, including the provision of power to the driver circuitries for the white LED chips, the UV LED chips, and the fan.

System electronics are shown in a first example in FIG. 5A. AC power provides a voltage Vac, which is provided to the white LED driver circuitry 92a, to the UV LED driver circuitry 92b, and to the fan 20. Although not shown, it should be understood that Vac may be processed (transformed, rectified to DC voltages, etc.) prior to being provided to the driver circuitries 92a and 92b and fan 20 in accordance with their input power needs. White LED driver circuitry 92a typically provides a compliance voltage Vw as necessary to provide a current Iw necessary to drive the white LED chips 28. A regulator 94a can be used to control Iw, as is well known. UV LED driver circuitry 92b is similar, and provides a compliance voltage Vuv as necessary to provide a current Iuv necessary to drive the UV LED chips 82, with a regulator 94b controlling Iuv. In one example, the power required by the fixture 10 may comprise about 100 Watts, with the white LED chips 28 requiring about 60 W, the UV LED chips 82 requiring approximately 30 W, and the fan requiring about 10 W.

It may be desired to separately control one or more aspects of the fixture 10. For example, it may be desired at a given time to drive only the white LED chips 28 to provide illumination to a room the fixture 10 is placed in, but to not drive the UV LED chips 82 to provide UV disinfection. Conversely, it may be desired at a given time (e.g., at night) to drive only the UV LED chips 82 to provide UV disinfection, but to not drive the white LED chips 28 to provide illumination. In this regard, the fixture 10 can include or be controlled by one or more switches 100, 102, or 104. For example, switch 100 comprises a master switch used to control all operations of the fixture, i.e., to control driving the white and UV LED chips 28 and 82, and the fan 20. Switch 102 can be used to independently control the white LED chips 28. Switch 104 can be used to independently control the UV LED chips 82 and the fan 20. Switch 104 is useful because it would normally be expected that the fan 20 and UV LED chips 82 would be enabled together, with the fan 20 drawing air flow into the UV sterilization box 14 that includes the chips 82. That being said, the UV LED chips 82 and fan 20 could also be independently controlled by their own switches. Any of the switches shown could comprise wall-mounted switches to which the fixture 10 is connected. Alternatively, the switches can appear in the light fixture (section 15) as part of the system electronics. In this respect, the switches may be controlled by a remote control, with system electronics including a wireless receiver (e.g., a Bluetooth receiver) for receiving input from the remote control. For example, application 200, explained further below, can be used to wirelessly control the switches.

System electronics can further include a safety switch 103. As described earlier, this switch 103 is designed to open to cut power to the UV LED chips 82 (e.g., via driver circuitry 92b) when the top cover 62 is removed from the UV sterilization box 14. As shown, safety switch 103 is in series with switch 104, and so would also disable power to the fan 20. However, switch 103 could also be located in the circuitry to cut power to only the LED driver circuitry 92b.

Figure 5B:
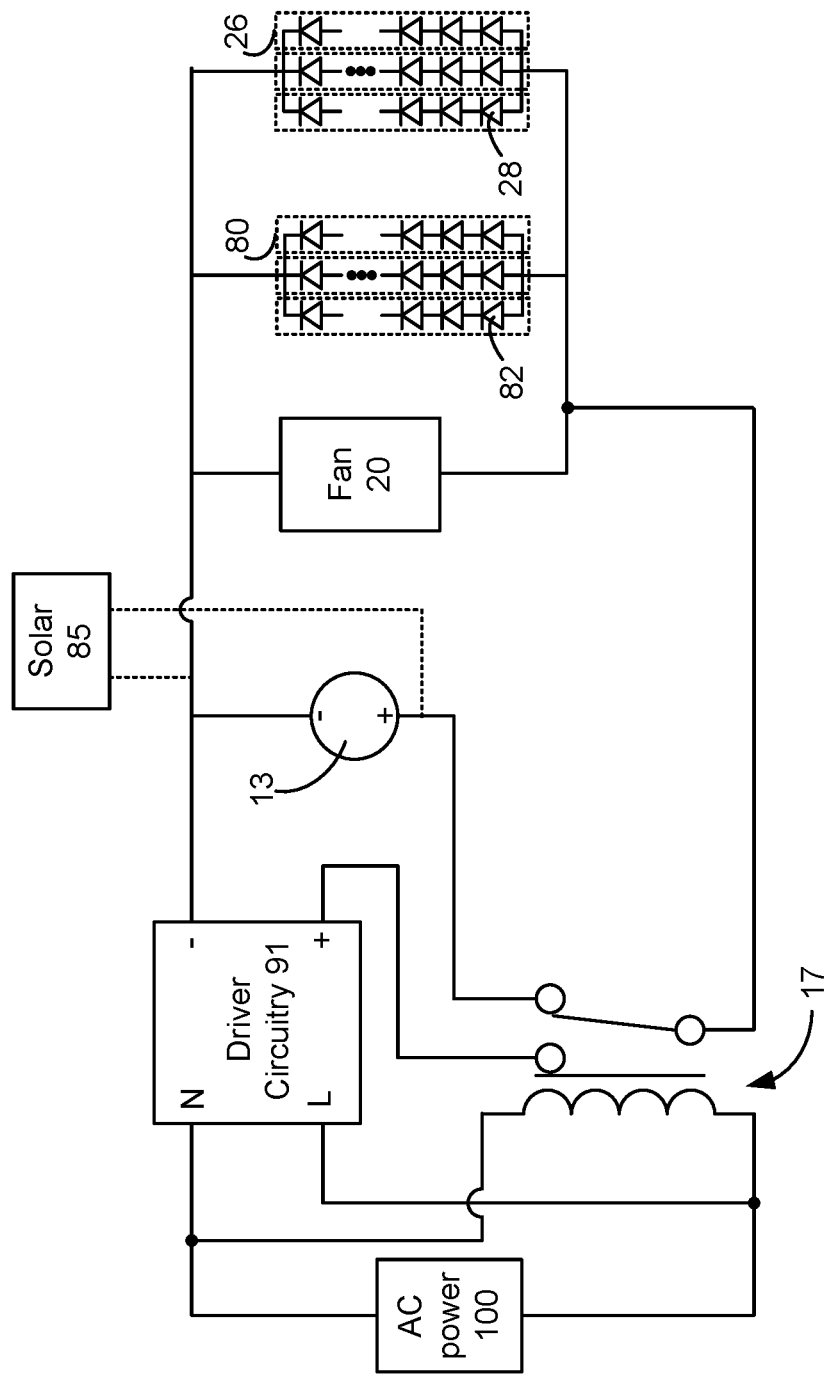

FIG. 5B illustrates another embodiment of system electronics. The system electronics allows the fixture 10 to be powered using either AC power 100 or using a battery 13, which would preferably be present in the electronic section 15 of the fixture 10. The battery 13 may be either a rechargeable battery or a primary battery. Though not shown in FIG. 5B, the system electronics may include charging circuitry for recharging the battery 13 when the fixture 10 is connected to AC power 100. The illustrated embodiment of the system electronics includes a relay 17, such as the illustrated single pole double throw (SPDT) relay, which is configured to automatically switch between battery 13 power and AC power 100 depending on whether AC power 100 is available. Other switching configurations will be apparent to a person of skill in the art. In FIG. 5B, the fan 20, the UV LEDs 82, and the white LEDS 28 are as described earlier. Driver circuitries 92a and 92b (FIG. 5B) are integrated as driver circuitry 91, which is also used to drive the fan 20. Note that the live (L) and neutral (N) terminals of the driver circuitry 91 are denoted in FIG. 5B. Various switches described in FIG. 5A are not shown in FIG. 5B for simplicity but could be present.

The system may also be provided a source of solar power 85. This source 85 may comprise solar panels included in a premise where the fixture 10 is installed, or which optionally is sold with the fixtures 10. Solar power from source 85 may power the fixtures 10, and also may be used to charge the batteries 13 in the fixtures. Again, the system may include battery charging circuitry, but this detail isn't shown in FIG. 5B. In this respect, AC power 100 isn't strictly necessary, and instead solar power can operate the fixtures 10 when the sun is present, leaving it to the batteries 13 to provide power when the sun isn't present.

Figure 6B:
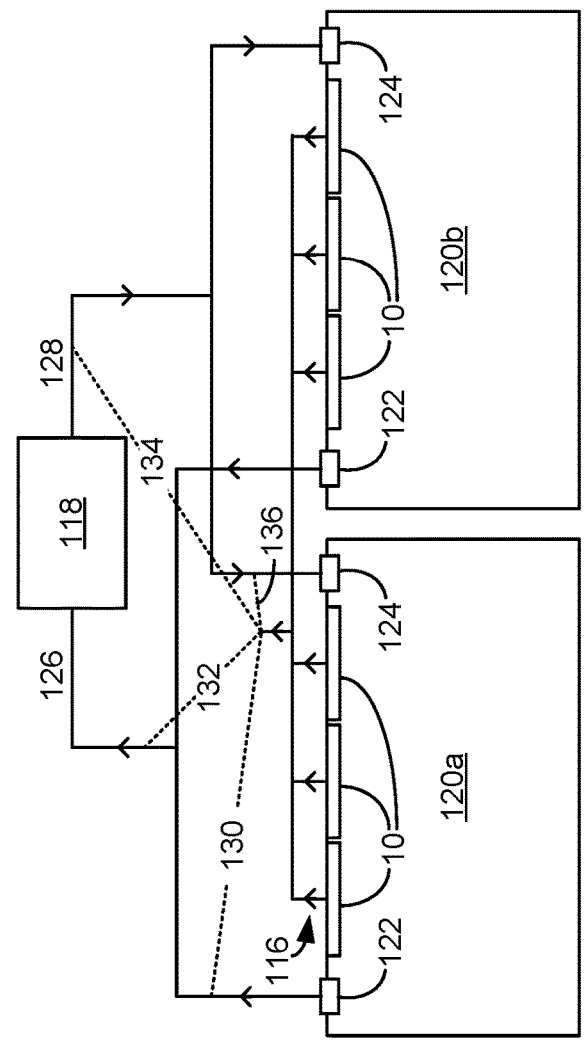
FIG. 6B shows that sterilized air outputs from the UV sterilization box can be combined.
Figure 6C:
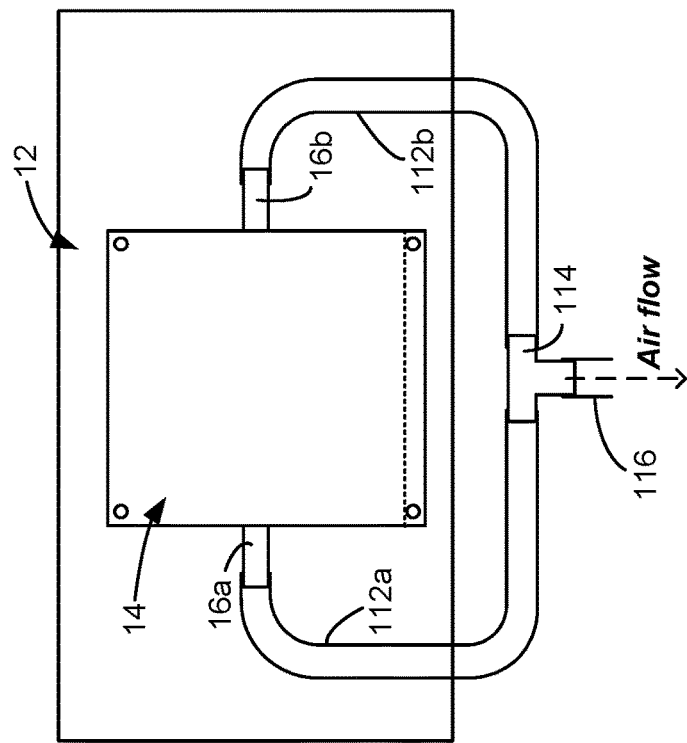
FIG. 6C shows how that sterilized air can be output into the air handling system of a building or house.

As discussed above, the UV sterilization box 14 includes one or more hose connectors 16a and 16b which output sterilized air, and such sterilized air is preferably distributed back into the room or building in which the fixture 10 appears. FIGS. 6A-6C show different examples of how this can occur. Sterilized air can also effectively be disposed with, such as by venting such air into the plenum space in a building or house, or through a vent to the outside environment.

FIG. 6A shows an example in which the sterilized air is output back into the room through the fixture 10 itself. In this example, which shows a larger light fixture (2×4 foot), the light box 12 includes one or more hose ports. Two such ports 110a and 110b are shown in FIG. 6A, and may comprise hose connectors allowing them to be joined to the hose connectors 16a and 16b by hoses 112a and 112b as shown. The ports 110a and 110b in this example proceed through holes in the back plane 50, the circuit board(s) 24, and the diffuser 40 of the fixture 10. Although not shown, the air output from the hose connectors 16a and 16b can be combined (e.g., FIG. 6B) and put back into the room through a single port 110 in the light box 12, or through more than two ports.

FIG. 6C shows that the air output from the hose connectors 16a and 16b can be placed into the air handling system in a building in which one or more fixtures 10 are placed, thus providing sterilized air to one or more rooms in the building. In this example, it is assumed that the building has a number of rooms (two of which 120a and 120b are shown) with each room having a number of fixtures 10 (three in each as shown). The building includes an air handler 118 with an input 126 and an output 128. One skilled will recognize that the duct work of an air handling system could include other components that are not shown, such as fans, exhaust vents, fresh air inputs, etc. Each room 120a and 120b has a supply vent 124 connected to the output 128 and a return vent 122 connected to the input 126. FIG. 6B shows that the air output from the hose connectors 16a and 16b in a given fixture 10 can be combined (e.g., FIG. 6B) using a junction 114, which outputs to an output hose 116. Junction 114 and output hose 116 could also be fit with filters (97) and valves (93, 95), as explained earlier with reference to FIG. 4. The outputs from several output hoses 116 can be connected as shown in FIG. 6C, and connected by another hose or duct work to any convenient point in the air handler duct system, including the return line of a given room (130), the input 126 to the air handler 118 (132), the output of the air handler 118 (134), or to the supply line of a given room (136). In any of these examples, the sterilized air is ultimately provided back into the room(s).

Figure 7:
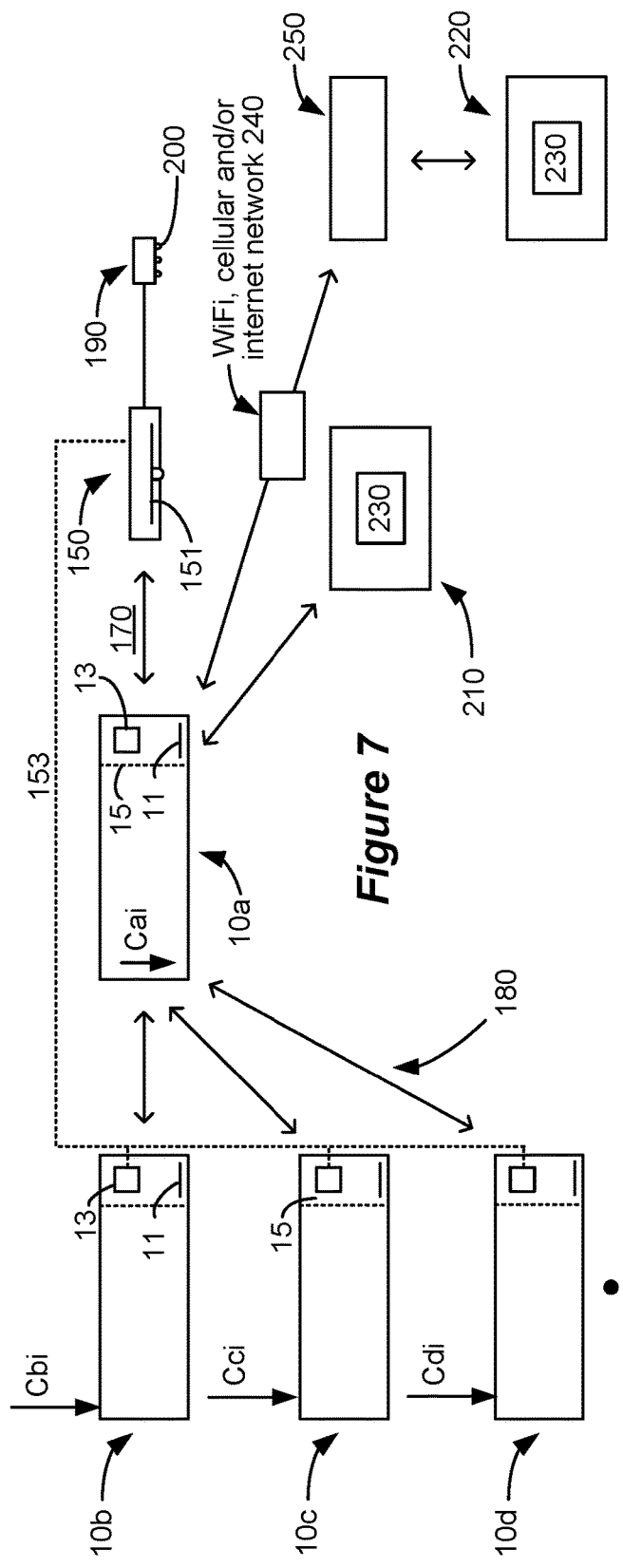
FIG. 7 shows a system of fixtures in an environment, which includes a sensor module for sensing environmental conditions and for allowing control of operation of the fixtures.

FIG. 7 shows further details by which one or more fixtures can be integrated and controlled in an environment, and further shows how environmental sensing can be included with the system. In this example, four fixtures 10a-10d are shown, which can be mounted in the ceiling of a room for example, as explained earlier. Also shown is a sensor module 150 which includes sensors that are used to sense various environmental conditions in the room. Such sensed conditions can be used to control various functions of the fixtures, such as operation of the fan 28, intensity of the UV LED chips 82s used for sterilization, and the intensity of the white LED chips 28 used for illumination, as explained further below.

The sensor module 150 can communicate with each of the fixtures 10i, either by electronic cabling or using a short range RF communication format such as Bluetooth™. In the depicted example, and more preferably, the sensor module 150 communicates with a particular one of the fixtures (10a) via communication link 170. This fixture 10a can be programmed in the system as a "master" fixture, while other fixtures (10b-10d) can be programmed as "secondary" fixtures, as explained further below. The master fixture 10a can operate a control algorithm 320 to control operation of the system, explained further below. The master fixture 10a can communicate with the secondary fixtures 10b-10d using electronic cabling, but again the use of short range RF communication links 180 such as Bluetooth is preferred. Preferably, the master and secondary fixtures are identical in construction and differ only in whether they are programmed as master or secondary fixtures.

The sensor module 150 may also communicate with an alert indicator 190, which includes one or more indicators such as LEDs 200 that can be used to provide certain visual alerts to persons in the environment indicative of environmental conditions that the sensor module has sensed. For example, the alert indicator 190 may indicate a green light is the sensor module 150 has not detected any unusual environmental conditions or if the system is otherwise working properly. The alert indicator 190 may indicate a red light if dangerous environmental conditions have been detected or if the system is not working properly. The alert indicator 190 may also indicate alerts in other ways. For example, the alert indicator 190 may include a speaker to audibly indicate alerts. A person seeing or hearing an alert at 190 may consult an application 230 to understand the details concerning the alert, as described further below. Although not shown, the alert indicator 190 may be integrated with the sensor module 150, with the sensor module 150 providing necessary alerts. However, because the alert indicator 190 may be distracting, it may be beneficial to place it in a non-obtrusive place, such as in the ceiling at a corner of a room. The sensor module 150 by contrast is preferably placed in the center of a ceiling of a room to most evenly sense the environment's conditions. The fixtures 10i would preferably be placed in the room as necessary to provide illumination and sterilized air, as described above. In the example shown in FIG. 7, the alert indicator 190 is hardwired to the sensor module 150, but these components could also communicate wirelessly (e.g., by Bluetooth).

Relevant electronics in the sensor module 150 are integrated on one or more circuit boards 151, while relevant electronics in the fixtures 10i are integrated on one or more circuit boards 11 preferably located in the electronics section 15 of the fixtures 10i, as explained earlier. Components present on circuit boards 151 and 11 are explained later with reference to FIG. 9.

As discussed earlier, each fixture 10 may each include a battery 13 for providing power to the fixtures. The output of these batteries 13 may be joined at a common power bus 153. Further, power bus 153 may be routed to the sensor module 150 to provide power to the sensor module 150. However, as explained further below, the sensor module 150 may also have its own battery 310.

Wireless communication in the system of FIG. 7 provides flexibility to allow the system to communicate with other devices to useful ends. For example, the system can communicate with an electronic device 210. This device 210 may be a general-purpose computing device such as a personal computer, tablet, smart cell phone and the like. Device 210 can run an application (app) 230 to allow a user to both control the system (illumination and/or UV sterilization), and to review important information reported from the system (such as alerts, or output from the sensors in the sensor module 150). Notice in the depicted example that the device 210 communicates with the master fixture 10a (again preferably using Bluetooth), although device 210 may also communicate with the sensor module 150 or other intermediaries in the system. The system (via master fixture 10a) can also communicate with other networks and systems. For example, via a Bluetooth router, the system may ultimately communicate with a Wifi™, cellular or internet network 240. Master fixture 10a may also include communication circuitry operable using WiFi™, cellular, or internet formats to allow connection to network 240 directly if necessary. Connectivity via such other networks 240 allows the system to be accessed via a remote device 220, which may again comprise a personal computer, tablet, smart cell phone and the like, and which may again run app 230 to allow for system control and monitoring.

Figure 8:
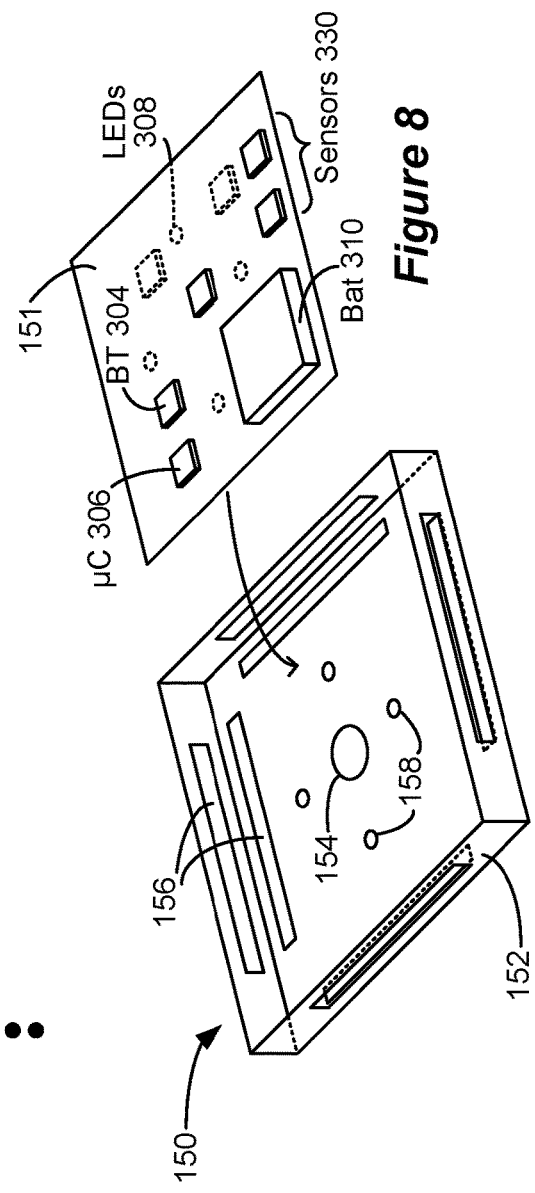
FIG. 8 shows details of the sensor module.

FIG. 8 shows the sensor module 150 in further detail. The module 150 includes a housing 152, which may be formed of plastic. The housing 152 may be formed with clips (not shown) allowing it to be secured to a bracket (not shown) affixable to a ceiling—similar to the manner in which a smoke detector is affixed to a ceiling. The control module 150 can also comprise a stand-alone device freely positionable in the environment being monitored. Within the housing 152 is the above-mentioned circuit board 151, which among other things includes various sensors 330 that monitor various environmental conditions, as explained further below. The housing 152 preferably includes air channels 156 to allow air in the environment to enter the sensor module 150 and come into contact with the sensors 330. Note that sensors 330 can be positioned on either side of the circuit board 151. Certain sensors described subsequently may require a line-of-sight to the environment being monitored, and in this regard the housing 152 can includes one or more openings 154 to allow such sensors to protrude through the housing and be directly exposed to the environment.

Figure 9:
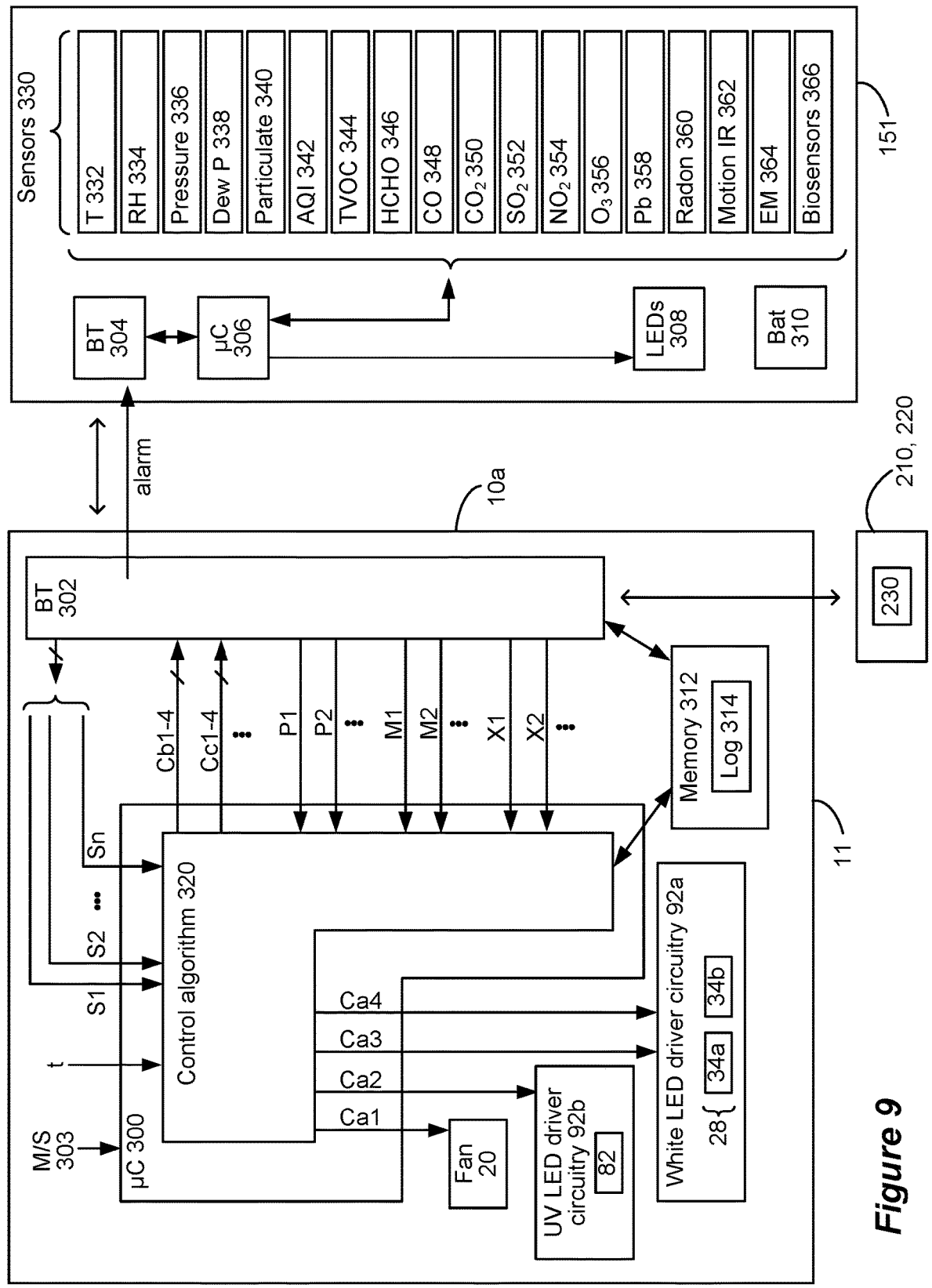
FIG. 9 shows components on circuit board within the sensor module and each of the fixtures.

Components present on circuit board 151 in the sensor module 150 are shown in FIGS. 8 and 9. As shown, the circuit board includes telemetry circuitry 304 to enable wireless communications with other devices, such as the master fixture 10a, and possibly also other devices such as devices 210 and 220 (FIG. 7). In one example, telemetry circuitry 304 comprises a communication antenna and chip sets designed for communications accordingly to a particular format, such as Bluetooth, WiFi, cellular, etc. In the depicted examples, telemetry circuitry 304 comprises a Bluetooth chip set and antenna. Circuit board 151 also preferably comprises controller circuitry 306 such as a microcontroller. A significant function of the controller circuitry 306 is to receive data being reported from the sensors 330, and to organize such data for communication, for example to the master fixture 10a.

Although not shown in FIG. 8, circuit board 151 in the control module 150 can be connected (plugged in) to a source of AC power (e.g., 100, FIG. 5), and circuit board 151 may include one or more rectifier/regulators to produce DC power to power the circuit board 151's various components. Additionally, or alternatively, the circuit board 151 can receive power from a battery 310. In a preferred example, the battery 310 is rechargeable, and is recharged (using AC power 100) by battery charging circuitry (not shown) on circuit board 151. Battery 310 may also comprise a permanent battery, requiring the user to replace the battery 310 once it is spent.

Providing a battery 310 in the sensor module 150 is preferred in case there is an interruption of AC power 100. In the case of a power interruption, the sensors 330 can continue to function, at least for a time (e.g., 90 minutes). Furthermore, battery 310 can provide a safety feature, and can allow the sensor module 150 to operate as an emergency illumination source. In this regard, the circuit board 151 can include one or more light sources, such as LEDs 308. These LEDs 308 (mounted to the underside of the circuit board 151) can protrude through openings 158 provided in the housing 152 to provide low-level illumination in the environment in case of a power outage. Further, illumination provided by LEDs 308 can also be controlled by a user of app 230, or LEDs 308 can illuminate automatically without user intervention, such as at certain times of day (e.g., after hours) or in accordance with information read from the sensors 330. For example, if the EM sensor 364 (FIG. 9) senses that the room is dark, perhaps because illumination in the fixtures 10i is off, controller circuitry 306 can activate the LEDs 308. LEDs 308 are hereinafter referred to as emergency LEDs 308, even though they do not necessarily illuminate during emergencies.

The sensor module 150 as mentioned can include a plurality of different sensors 330, each designed to detect a particular condition of the environment in which the sensor module is placed. For example, and as shown in FIG. 9, the sensor module 150 can include:

- a temperature sensor 332;
- a relative humidity sensor 334 (e.g., part number HTS221, manufactured by STMicroelectronics. This part also includes a temperature sensor 332);
- an atmospheric pressure sensor 336;
- a dew point sensor 338;
- a particulate sensor 340 (e.g., part number SN-GCJA5, manufactured by Panasonic Photo & Lighting Co., Ltd.);
- an Air Quality Index (AQI) sensor 342;
- a Total Volatile Organic Compound (TVOC) sensor 344 (e.g., part number ZMOD4410, manufactured by Renesas Electronics Corp. This part also includes an AIQ sensor 342 and a $CO_2$ sensor 350);
- an HCHO (formaldehyde) sensor 346;

a carbon monoxide (CO) sensor 348 (e.g., part number SGX-4CO, manufactured by SGX Sensortech);

a carbon dioxide ($CO_2$) sensor 350 (e.g., part number Telaire T6703, manufactured by Telaire Co.);

a sulphur dioxide ($SO_2$) sensor 352;

a nitrous dioxide ($NO_2$) sensor 354;

an ozone ($O_3$) sensor 356;

a lead (Pb) sensor 358;

a radon (Rn) sensor 360;

an infra-red (IR) motion sensor 362 (e.g., part number EKMB130911, manufactured by Panasonic, Inc.);

an ElectroMagnetic (EM) sensor 364, which can be used to assess the spectrum of electromagnetic radiation in the environment; and biosensors 366, which can use to determine whether pathogens are present in the environment, including bacteria, viruses, fungi and the like.

Preferred part numbers for some of these sensors 330 are listed above, although one skilled will recognize that there are many different types of these sensors. It is not required that the sensor module 150 have all of the above-listed sensors: certain of these sensors 300 may only be important in particular environments (e.g., manufacturing environments) and therefore may not be necessary when sensor module is used in different environments (e.g., office environments). The above sensors 330 preferably output values indicative of the quantity of the conditions they are sensing, although certain sensors may operate in a binary fashion and only output whether or not a particular condition has been sensed. Possible sensors 330 as shown in FIG. 9 are not an exhaustive list, and sensor module 150 can include still other environmental sensors presently existing or developed in the future. In one example, a sensor module 150 can include all possible sensors 330 potential customers might desire, with the manufacturer programming the sensor module 150 (e.g., using app 230, FIG. 12) to only enable sensors 330 relevant to a particular customer or environment. As mentioned above, sensors 330 requiring a line of site to the environment can be placed in an opening 154 (FIG. 8) of the sensor module's housing 152, such as the IR motion sensor 362.

FIG. 9 also shows components present on the circuit board 11 for each of the fixtures 10$i$. The circuit board 11 includes controller circuitry 300 (e.g., a microcontroller), which is programmed with a control algorithm 320, explained further below. The controller circuitry 300 receives a master/secondary (M/S) input 303 which informs whether the fixture 10$i$ in which circuit board 11 is placed is to operate as a master (e.g., 10$a$) or a secondary (10$b$-10$d$) fixture. By programming the M/S input 303 accordingly, a master fixture will be configured to receive information from the sensor module 150, and to control the secondary fixtures using the control algorithm 320. By contrast, programming the M/S input 303 to designate a fixture as a secondary fixture will configure that fixture to only communicate with and be controlled by the master fixture 10$a$. Thus, the control algorithm 320, if programmed into the controller circuitry 300 of a secondary fixture, will be disabled. In one example, the M/S input 303 may comprise a dip switch or button which may be set in each fixture 10$i$ by the manufacturer or the customer. Alternatively, the M/S input 303 may be set wirelessly using devices 210 and 220 via app 230 (FIG. 7). It is assumed in FIG. 9 that the circuit board 11 has been programmed at M/S input 303 to operate as a master.

Circuit board 11 includes telemetry (e.g., Bluetooth) circuitry 302 capable of receiving information wirelessly transmitted from the sensors 330 in sensor module 150 and communicating with the other fixtures 10$i$. Environmental conditions sensed by the sensors 330 are denoted as S1, S2, S3, etc., in FIG. 9, each representing different reported sensed condition (e.g., temperature, humidity, pressure, dew point, particulates, etc.). Such sensor information is received at control algorithm 320 programmed into controller circuitry 300. The control algorithm 320 operates to control different aspects of the fixtures 10$i$ by issuing various control signals, C.

In a preferred example, a number of different control signals C are issued for each fixture 10$i$. For example, control signals Cai comprise control signals for fixture 10$a$, with Ca1 controlling the fan 20 (e.g., whether it is on or off, and the speed of the fan), Ca2 controlling the UV LED chips 82 (e.g., whether they are on or off, and their intensity), and with Ca3 and Ca4 controlling the white LED chips 28 (again whether they are on or off, and their intensity). Specifically, Ca3 can control the LEDs 34$a$ (e.g., peaking at 405 nm; see FIGS. 2A & 2B), while Ca4 controls LEDs 34$b$ (e.g., peaking at 405 nm). Because the fixture in FIG. 9 has been programmed to act as a master fixture, notice that these control signals Cai can be sent by wiring to the appropriate hardware components in this fixture. Thus, fan 20 receives Ca1, UV LED driver circuitry (92$b$) driving UV LED chips 82 receives Ca2, and white LED driver circuitry 92$a$ driving white LED chips 28 (LEDs 34$a$ and 34$b$) receives Ca3 and Ca4. Such driving circuitry is shown on circuit board 11, but could be present on a different circuit board in the fixture. One skilled will understand that these control signals Cai as output from the control algorithm 320 may be processed as necessary to interface with the hardware components that they control.

The control algorithm 320 also determines control signals C necessary for each of the secondary fixtures (e.g., 10$b$-10$d$), and uses the telemetry circuitry 302 to wirelessly transmit those control signals to those fixtures. For example, control signals Cbi (Cb1 for the fan, Cb2 for UV LED chips 82, and Ca3 and Ca4 for white LED chips 28) are to transmitted to fixture 10$b$, control signals Cci are transmitted to fixture 10$c$, and so on. Again these control signals may undergo some processing at the receiving fixtures as necessary to interface with their hardware components. Thus, control of all fixtures 10$i$ in the system is provided by the control algorithm 320 in the programmed master fixture 10$a$. Such control in certain circumstances can occur in accordance with the information Si that are sensed by the various sensors 330 in the sensor module 150, as explained further below.

The control algorithm 320 may also receive an indication of the present time and date, designated as 't,' which may be provided from clocking circuitry on the circuit board 11. Knowing the present time can be useful in the system for a number of different reasons. For example, and as discussed further below, the control algorithm 320 may be programmed take different actions at different times of day. Furthermore, the circuit board 11 may also include a memory 312 which keep a log file 314 logging important events that occur during operation of the system, and entries in the log file 314 may be time stamped with the time/date t. The log file 314 may be reviewable by a user using the app 230 on devices 210 or 220 (FIG. 7), as explained further below. The log file 314 for example may store information Si reported by the sensors 330, thus allowing the user to review the current value of these sensor outputs or how they are varying as a function of time. The log file 314 may also store information regarding the various control actions that algorithm 320 has undertaken (e.g., the status of control signals C), which may also be reviewed as a function of time.

The control algorithm 320 may receive a number of inputs to control its operation, in addition to the sensor inputs Si. For example, the control algorithm 320 may receive one or more programs Pi, which may specify how control algorithm will control the various fixtures 10*i* in terms of illumination, UV sterilization functionality, and fan operation. A program may contain information that allows the control signals C to be determined for each hardware component in each fixtures 10*i*. A program Pi may also include timing (e.g., a schedule) during which it will operate.

The control algorithm 320 can also operate automatically to control illumination and disinfection in the system dependent on what the sensors 330 sense (Si). In this regard, the control algorithm 320 can be programmed with a number of parameters Xi, which dictate how the control algorithm 320 will operate. Parameters Xi may comprise thresholds for certain sensed information Si, or weights that the control algorithm 320 may apply to such sensed information. Parameters Xi may also include variables that allow the control algorithm 320 to make automatic adjustments based on a history of use of the system, and as such the control algorithm 320 may comprise a machine learning algorithm, which parameters Xi comprising inputs to the machine learning algorithm. Programs Pi and parameters Xi may programmed into control algorithm 320 by the system manufacturer, or may also be wirelessly programmed using the application 230 on devices 210 and 220 for example.

Figure 10:
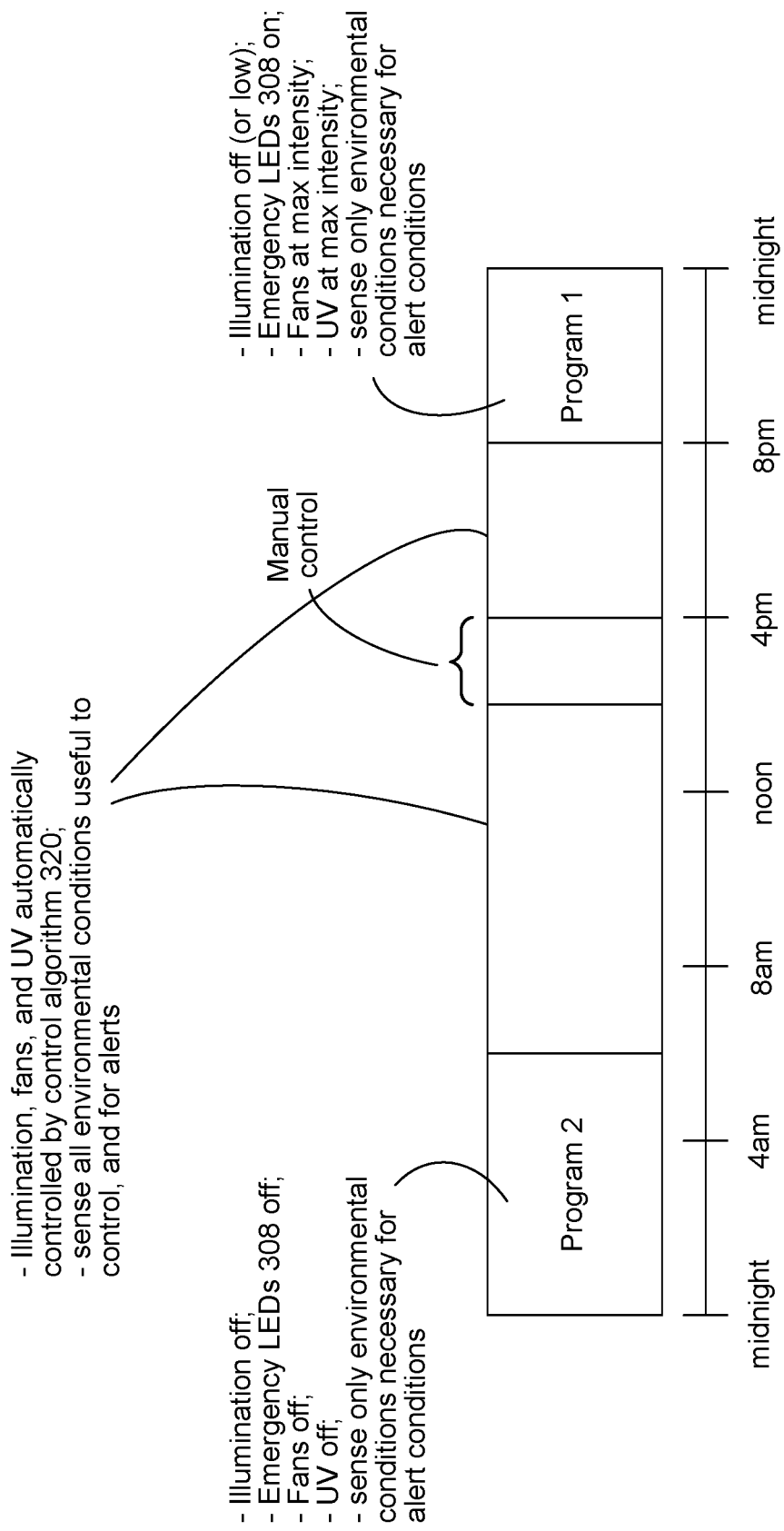
FIG. 10 shows an example of various manner by which the fixtures can be controlled using a control algorithm.

FIG. 10 shows a simple example of different ways that the system can be controlled at different points in time. In this example, it is assumed that control varies during a day, but longer periods of time (weeks, months) etc., could also controlled. Using longer periods may be sensible, as needs for system control may vary on weekends or holidays, or in hotter or colder months for example. The example in FIG. 10 assumes that the system is installed in an office conference room, although again this is merely an example as the system can be used in other environments (industrial, greenhouse, etc.) as well.

Two programs P1 and P2 are specified for use at different time periods. Program 1 operates at the end of a work day, from 8 pm to midnight in this example. Because people would not be expected to be present during these hours, program 1 specifies that illumination provided by the fixtures (white light LEDs 28) should be off (or low). Although not shown in FIG. 10, program 1 may also allow illumination when people are detected in the room, e.g., by motion IR sensor 362 (FIG. 9). Emergency LEDs 308 on the sensor module 150 may be illuminated to provide low level lighting. It may be reasonable to well sterilize the air in the room at the end of a work day, and program 1 sets fans 20 and UV sterilization (provided by UV LEDs 82) in the fixtures 10*i* to a maximum intensity. During program 1, sensed environmental conditions are not important to control of the system, and hence may be ignored by the control algorithm 320 (except perhaps the output from motion IR sensor 362). However, such environmental conditions can continue to be sensed, and if necessary alerts regarding certain environmental conditions (in particular, those that present dangers, such as CO, $O_3$, Pb, Rn, etc.) can be generated by the control algorithm 320. Such alerts can be transmitted to the sensor module 150 and in turn to the alert indicator 190 (FIG. 7), as well as to devices 210 and 220 where the nature of the alert can be viewed in the application 230.

Program 2 runs from midnight to 6 am. At this point, illumination may be of lesser concern, and so illumination provided by the fixtures 10*i* may be programmed off (even if motion is detected by motion IR sensor 362). Likewise, emergency LEDs 308 in the sensor module 150 may be off. Finally, because the air was earlier well sterilized during program 1, fans and UV sterilization may be programmed as off during program 2. As with program 1, sensed environmental conditions may not be important to control of the system during program 2, and hence may be ignored by the control algorithm 320, except to issue alerts.

From 6 am to 8 pm, generally corresponding to work hours, a specific program may not run. Instead, illumination, fans, and UV sterilization may be automatically controlled by the control algorithm 320 in accordance with sensed environmental conditions. (Providing automated control via the control algorithm 320 may also comprise a "program," e.g., program 3). It may be sensible to provide automated control during this time period because environmental conditions in the conference room may be changing significantly. As noted above, automatic operation of the control algorithm 320 can in one example be controlled using parameters Xi, which may comprise thresholds for certain sensed information Si, or weights that the control algorithm 320 may apply to such sensed information.

Figure 11:
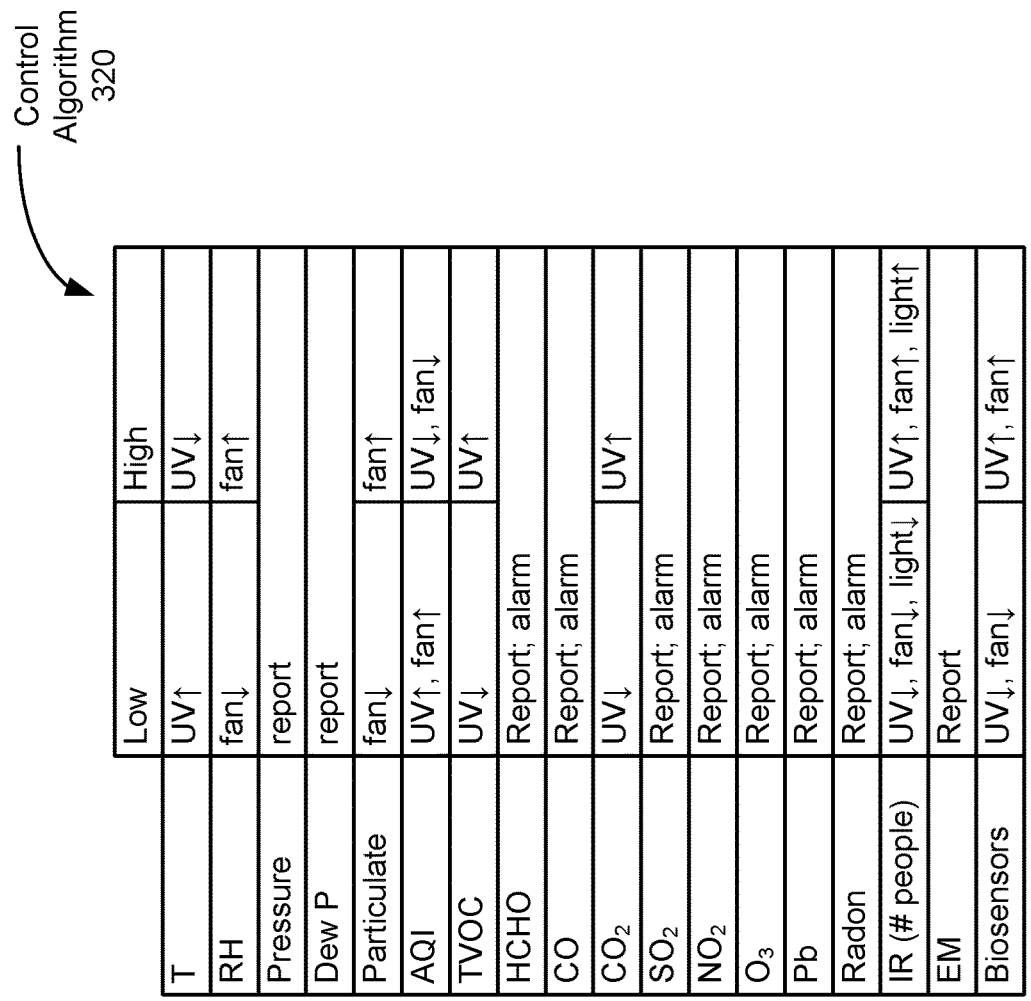
FIG. 11 shows example of how various sensed environmental conditions can be used to control various functions of the fixtures (e.g., illumination, UV, and fan speed).

FIG. 11 generally explains how various sensed environmental conditions can be used by control algorithm 320 to provide control in the system. For example, temperature (T) (sensor 332) can affect pathogens such as viruses, bacteria, and fungi, because such pathogens are less inhibited at lower temperatures and more inhibited (and perhaps even eradicated) at higher temperatures. As such, it may be reasonable for the system to provide higher intensity UV radiation at lower temperatures (below a temperature threshold X1), and to provide lower intensity UV radiation at higher temperatures (above X1).

Alternatively, the sensed temperature can be weighted (along with other sensed environmental conditions) to determine how UV sterilization in the system should be controlled. Weights can be useful as a control mechanism, because they can quantify how significantly a particular sensed environmental condition should be treated relative to the system function being controlled. For example, assume temperature is accorded a low weight X1 relative to UV sterilization. A different environmental condition, such as the amount of detected Total Volatile Organic Compounds (TVOC) (sensor 344), may be accorded a higher weight X2 relative to UV sterilization because higher amounts of UV radiation may break down such compounds. If the sensed temperature is high (suggesting that UV sterilization should be decreased), and the sensed amount of TVOCs is also high (suggest that UV sterilization should be increased), the system may be in conflict as to whether UV sterilization should be decreased or increased. However, the different weights (X1 and X2) in this circumstance would suggest that the control algorithm 320 increase UV radiation. In effect, control algorithm 320 gives greater weight to sensed TVOCs over sensed temperature when deciding how to control UV sterilization.

Different sensed environmental conditions may impact the control of different control functions in the system. For example, while temperature is relevant to adjusting the intensity of UV, it may not be relevant to adjustment of the fans or the illumination. By contrast, relative humidity (RH) (sensor 334) is relevant to controlling the fans 20 in the fixtures: if the RH is low, the speed of the fans 20 can be decreased, but if RH us high, the speed of the fans may need to be increased to promote the flow of moist (heavy) air into the fixtures. Other sensed environmental conditions may be relevant to illumination control. For example, the motion IR sensor 362 may determine the number of persons present in the conference room, and increase (or turn on) the illumination when one or more persons are detected. Some sensed environmental conditions may be relevant to control of more than one function in the system. For example, the motion IR sensor 362 may also control the fan and UV sterilization, increasing both when the number of persons in the room is high, and decreasing both when the number is low.

Still other sensed environmental conditions may not be used by the control algorithm 320 for system control, but instead may only be recorded and reported, or used to issue alerts. For example, the detection of lead (Pb sensor 358) may not be relevant to adjustment of illumination, fans, or UV sterilization, and thus may not be used for system control. However, because lead is dangerous, it can trigger an alert (e.g., at alert indicator 190), and may be logged (314, FIG. 9) for user review at devices 210 or 220. Still other sensed environment conditions may simply be logged and reported, but not used to set any alarms (e.g., atmospheric pressure, dew point, sensed EM spectra, etc.).

Returning again to FIG. 10, automatically control by the control algorithm 320 in accordance with sensed environmental conditions generally occurs from 6 am to 8 pm. However, such automated control may be interrupted during a period of manual control, as shown from 2 pm to 4 pm. During this time period (perhaps corresponding to a large meeting in the conference room), a user may have used app 230 on devices 210 or 220 for example to manually control one or more functions in the system. For example, during manual control, the user may have decided to provide maximum illumination, maximum UV sterilization, or maximum fan speed, or none at all, thus overriding what control algorithm 320 would otherwise automatically suggest. During manual control, the user may also program the various fixtures to operate differently. Manual control is represented in FIG. 9 by inputs Mi, received from the devices 210 or 220, which may correspond to a user selection of the various control signals C for the various fixtures. Note also during manual control that a user may choose to run a particular program for an unscheduled amount of time. It is assumed in FIG. 10 that the user has caused the control algorithm 320 to return to automatic control at the end of the meeting (e.g., at 4 pm), although the control algorithm 320 may also automatically return to its schedule at some default time after manual control was engaged. Lastly, although not shown, note that programmed/manual control and automated control may not be mutually exclusive in the system. For example, control algorithm 320 may provide for automated control of UV sterilization and the fans in the system, leaving illumination functionality subject to manual or programmed control.

Figure 12:
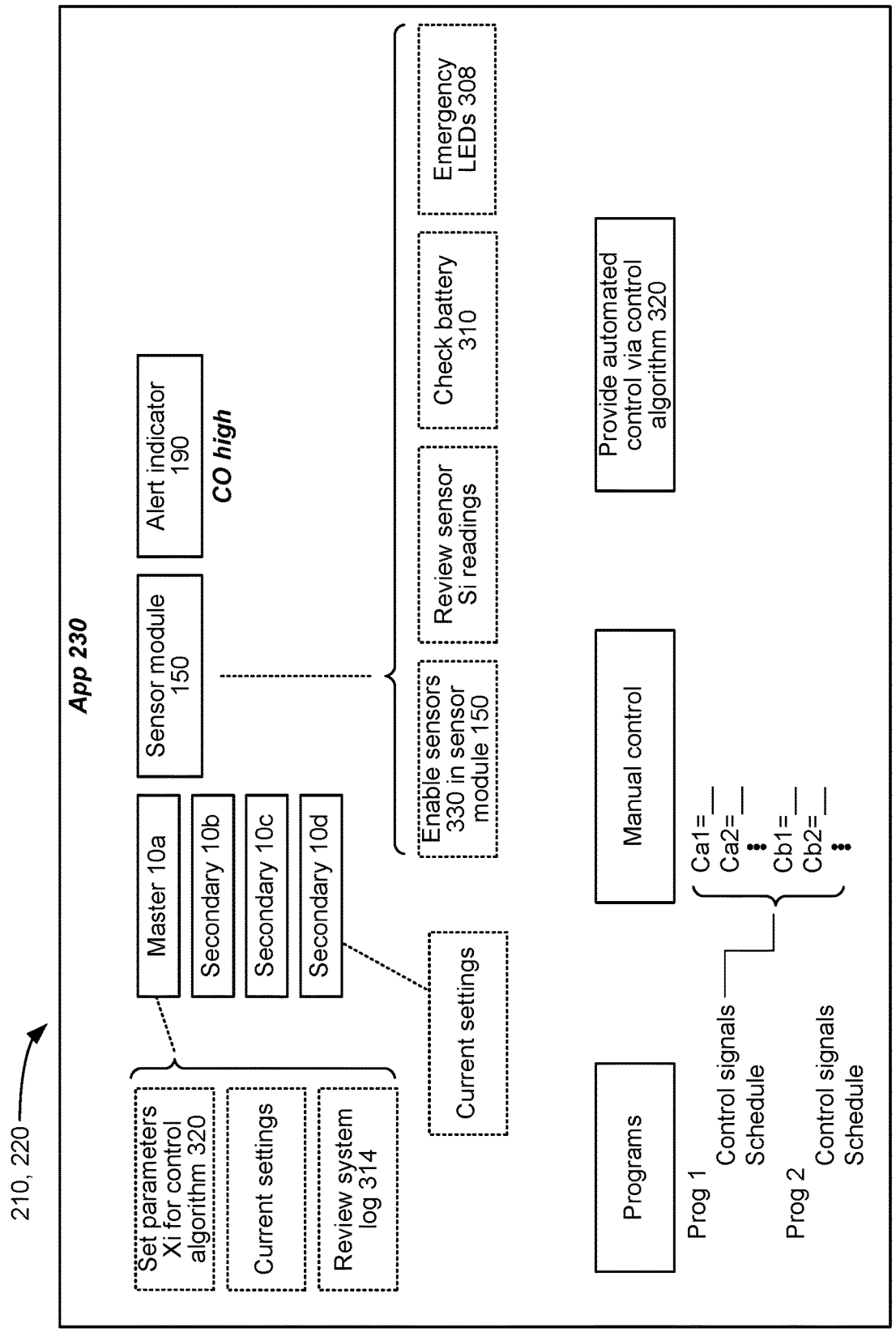
FIG. 12 shows a graphical user interface on an application executable on a wireless device for controlling and monitoring the system.

An example of a graphical user interface (GUI) for application 230 as may nm on devices 210 or 220 is shown in FIG. 12. As noted earlier, application 230 can be used by a user to control the system, and to review status information reported by the system. In the example shown in FIG. 12, each of the system's components is shown in the application, including the various fixtures 10i, the sensor module 150, and the alert indicator 190. Preferably, each of the displayed components can be selected in the GUI to display additional information about the component and/or to allow for data to be input. For example, selecting the master fixture allow for the control algorithm 320 operative in this component to be programmed, for example by allowing the parameters Xi discussed above to be input. Selecting the master fixture also allows the log file 314 to be reviewed. Further, selecting any of the fixtures 10i (master or secondary) allows the current settings at that fixture (e.g., illumination, fan, UV—e.g., their control signals C) to be reviewed.

Selecting the sensor module 150 provides further options to allow various sensors 330 in the sensor module 150 to be enabled. As noted above, not all sensors 330 provided by sensor module 150 may be necessary to use in a given environment. Selection of the sensor module 150 also allows the current sensor outputs Si to be reviewed, although this may also be reviewable via the log file 314. Selecting the sensor module 150 can also provide an option for to allow a user to review the status of the battery 310 in the module, such as how full this battery is and/or how much more operating time is remaining. Lastly, selecting the sensor module 150 allows a user to review the status (e.g., on/off) of the emergency LEDs 308, and can also allow the user to turn these LEDs on or off (or to adjust their intensities).

The alert indicator 190 preferably displays alerts determined by the system even without selection by the user. In the depicted example, an alert has issued because the sensor module 150 has sensed an excess of carbon monoxide. Displayed alerts may be selectable to allow the user to review further details information (such as the exact level of carbon monoxide detected).

The application 230 preferably also includes options to allows various programs to be set, named, and if necessary scheduled for use at particular times. Definition of a program can include input of any of the control signals necessary at any of the fixtures 10i, including fan speed (Cai), UV LED chip 82 intensity (Cbi), and white LED chip intensity (Cci and Cdi). These control signals are shown in conjunction with a manual control option, whereby any of these control signals can be individually changed by the user at any time, thus overriding the current programming of the system. Lastly, the application 230 can include an option to allow for automated control of the system via the control algorithm 320. As discussed above, such automatic control occurs in accordance with one or more environmental conditions that are sensed by the sensors 330 in the sensor module. One skilled in the art will realize that there are many different ways in which information may be organized for input to, or output from, the GUI in the application 230, and FIG. 12 is therefore merely one example.

Figure 13:
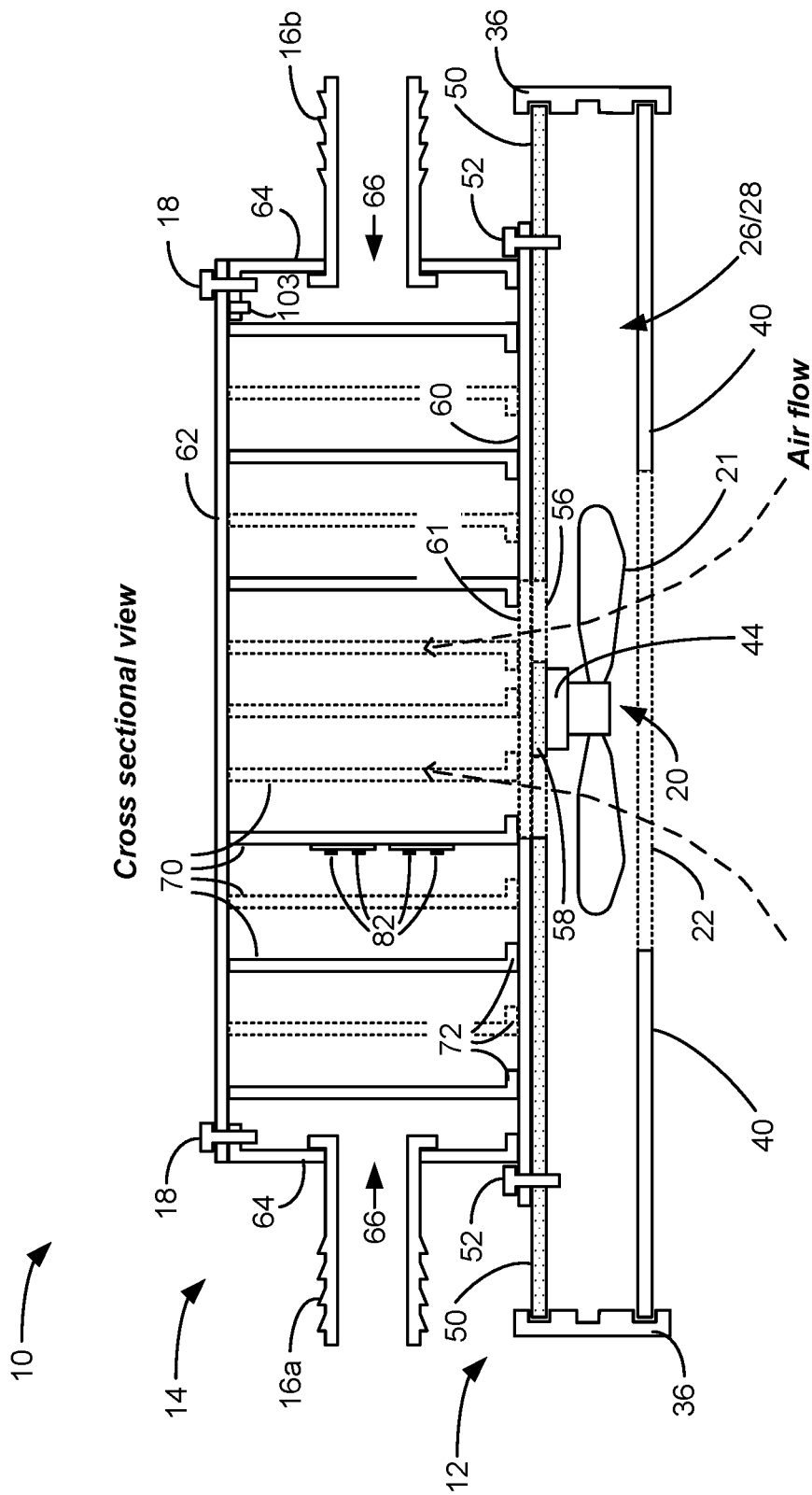
FIG. 13 shows an alternative for the fixture which provides only for UV sterilization and air circulation, but not illumination.

To this point, it has been assumed that the fixtures 10 provide both illumination (e.g., using white LED chips 28) and sterilization (e.g., using UV LED chips 82). However, this is not strictly necessary. As shown in FIG. 13, a fixture 10 may only comprise hardware components necessary to provide sterilization (e.g., the UV LED chips 82, the fan 20), etc. That is, fixture 10 may not necessarily provide for illumination. This is still beneficial, because ceiling-mountable fixtures like that shown in FIG. 13 can still provide UV sterilization to the environment in which the fixture is placed. A fixture of this sort may be particularly useful if the environment in question already has its own illumination sources.

Many modifications to the disclosed fixture 10 can be made, and the fixture 10 can be used in different environments to useful ends. For example, the white LED chips 28 may not include significant peaks at either or both of 405 nm or 470 nm, although the inclusion of these wavelengths is preferred to further aid sterilization that the fixture 10 provides. In fact, the white LED chips 28 may not be used, and instead other white light sources (e.g., bulbs) could be used in the fixture 10, with disinfection occurring strictly through use of the fan 20 and the UV sterilization box 14. The UV sterilization box 14 could include UV radiation sources other than UV LED chips 82. For example, various UV emitting bulbs could be used inside the UV sterilization box 14.

The fixture 10 and system can be used in environments where pathogens may be present, and in particular air borne pathogens. This can include hospitals, nursing homes, operating rooms, restrooms, kitchens, etc. Fixture 10 can also be used in a grow farm setting, in which light fixtures 10 are used to grow plants. For example, the disclosed fixture can be used in the context of the above-incorporated '900 patent, and can include the various improvements to a light fixture that are disclosed in that document.

The disclosed fixture 10, and/or the sensor module 150, may be made portable, as disclosed in "Portable Disinfection Unit," by inventors John C. Higgins, Cody Renwick, Tim Gray, and Chris Fall, a patent application which is filed concurrently herewith [Ser. No. 17/317,669], and which is incorporated herein by reference in its entirety.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system positionable in an environment, comprising:
    a sensor module comprising
        a plurality of sensors each configured to sense different environmental conditions in the environment, and
        first telemetry circuitry configured to wirelessly transmit the sensed environmental conditions; and
    a master fixture comprising
        second telemetry circuitry configured to wirelessly receive the transmitted sensed environmental conditions;
        a fan configured to draw air from the environment into the fixture; and
        a sterilization box configured to receive the drawn air and to output sterilized air for inclusion back into the environment, wherein the sterilization box comprises a plurality of ultra violet (UV) radiation sources configured to irradiate the drawn air with UV radiation along at least one path to produce the sterilized air;
        illumination sources configured to provide illumination to the environment, wherein the illumination sources emit light at a peak wavelength of approximately 405 nm and a second next-highest peak wavelength of approximately 470 nm to simultaneously disinfect the environment and provide human-safe lighting, wherein the illumination sources are distinct from the UV radiation sources; and
        controller circuitry configured with a control algorithm to automatically control the fan and the UV radiation sources in accordance with the sensed environment conditions.

2. The system of claim 1, wherein automatically controlling the fan and the UV radiation sources comprises simultaneously adjusting a speed of the fan and adjusting an intensity of the UV radiation sources.

3. The system of claim 1, wherein the control algorithm is configured to automatically and simultaneously control the fan, the UV radiation sources, and the illumination sources in accordance with the sensed environment conditions.

4. The system of claim 3, wherein automatically controlling the fan, the UV radiation sources, and the illumination sources comprises one or more of: turning on or off the fan; adjusting a speed of the fan; turning on or off the UV radiation sources; or adjusting an intensity of the UV radiation sources; turning on or off the illumination sources; or adjusting an intensity of the illumination sources.

5. The system of claim 1, wherein the fixture comprises:
    at least two holes for outputting sterilized air,
    an air flow path from the fan to each hole, and wherein at least one air flow path is non-linear.

6. The system of claim 1, wherein the UV radiation sources comprise UV LED chips configured to produce the UV radiation with a peak wavelength in the range from 200 to 280 nm.

7. The system of claim 1, wherein the sensor module and the master fixture are configured to be affixed to a ceiling in the environment.

8. The system of claim 1, wherein the sensor module further comprises a battery.

9. The system of claim 8, wherein the sensor module further comprises white LEDs to provide illumination to the environment, wherein the white LEDs are configured to receive power from the battery.

10. The system of claim 1, further comprising an alert indicator, wherein the control algorithm is configured to issue an alert to be broadcast by the alert indicator depending on the sensed environment conditions.

11. The system of claim 1, further comprising an application configured to be executed on an external device in wireless communication with the master fixture, and to generate a graphical user interface on the external device.

12. The system of claim 11, wherein the application is configured to receive at the graphical user interface a user input to initiate the control algorithm to automatically control the fan and the UV radiation sources in accordance with the sensed environment conditions.

13. The system of claim 12, wherein the application is further configured to receive at the graphical user interface one or more inputs to cause the control algorithm to manually control the fan and the UV radiation sources in accordance with the one or more inputs.

14. The system of claim 12, wherein the application is further configured to receive at the graphical user interface a user selection of a program to cause the control algorithm to control the fan and the UV radiation sources in accordance with the selected program.

15. The system of claim 1, further comprising one or more secondary fixtures identical in construction to the master fixture but differently programmed from the master fixture, each secondary fixture also comprising:
    second telemetry circuitry;
    a fan configured to draw air from the environment into the fixture; and
    a sterilization box configured to receive the drawn air and to output sterilized air for inclusion back into the environment, wherein the sterilization box comprises a plurality of ultra violet (UV) radiation sources configured to irradiate the drawn air with UV radiation along at least one path to produce the sterilized air.

16. The system of claim 15, wherein the control algorithm in the master fixture is configured to automatically control the fan and the UV radiation sources in the master fixture and the one or more secondary fixtures in accordance with the sensed environment conditions.

17. The system of claim 16, wherein the second telemetry circuitry in the master fixture is further configured to wirelessly transmit one or more control signals to each of the secondary fixtures to automatically control the fan and the UV radiation sources in the one or more secondary fixtures.

18. The system of claim 17, wherein the second telemetry circuitry in each of the one more secondary fixtures is configured to receive the one or more control signals.

19. The system of claim 15, wherein the primary fixture and the one or more secondary fixtures further comprise illumination sources configured to provide illumination to the environment, wherein the control algorithm is configured to automatically control the fan, the UV radiation sources, and the illumination sources in the primary fixture and each of the one or more secondary fixtures in accordance with the sensed environment conditions.

20. The system of claim 1, wherein the fan draws air simultaneously into at least two different air flow paths within the fixture.

21. The system of claim 1, wherein the fan is a single fan that draws air simultaneously into at least four different air flow paths within the fixture.

22. The system of claim 1, wherein one or more of the at least one path comprises a portion of the path comprising an entry and exit, the entry and exit being the same, the portion defined by three or more baffles, the portion comprising a plurality of UV radiation sources, and the portion creating a vortice in the air flow path.

* * * * *